US009949042B2

(12) United States Patent
Goorevich et al.

(10) Patent No.: US 9,949,042 B2
(45) Date of Patent: *Apr. 17, 2018

(54) AUDIO PROCESSING PIPELINE FOR AUDITORY PROSTHESIS HAVING A COMMON, AND TWO OR MORE STIMULATOR-SPECIFIC, FREQUENCY-ANALYSIS STAGES

(71) Applicant: Cochlear Limited, Macquarie University, NSW (AU)

(72) Inventors: Michael Goorevich, Naremburn (AU); Paul Holmberg, Sydney (AU); Adam Hersbach, The Patch (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/296,605

(22) Filed: Oct. 18, 2016

(65) Prior Publication Data

US 2017/0041721 A1    Feb. 9, 2017

Related U.S. Application Data

(63) Continuation of application No. 14/524,377, filed on Oct. 27, 2014, now Pat. No. 9,510,114, which is a continuation of application No. 13/649,494, filed on Oct. 11, 2012, now Pat. No. 8,873,770.

(51) Int. Cl.
| | |
|---|---|
| *H04R 25/00* | (2006.01) |
| *A61N 5/06* | (2006.01) |
| *H04R 3/00* | (2006.01) |
| *A61N 1/36* | (2006.01) |
| *G10L 21/0208* | (2013.01) |

(52) U.S. Cl.
CPC ....... *H04R 25/505* (2013.01); *A61N 1/36036* (2017.08); *A61N 5/0622* (2013.01); *H04R 3/005* (2013.01); *H04R 25/606* (2013.01); *G10L 21/0208* (2013.01); *H04R 2225/43* (2013.01); *H04R 2225/67* (2013.01); *H04R 2430/03* (2013.01)

(58) Field of Classification Search
CPC combination set(s) only.
See application file for complete search history.

(56) References Cited

U.S. PATENT DOCUMENTS

| | | | |
|---|---|---|---|
| 6,611,718 | B2 | 8/2003 | Zilberman et al. |
| 2006/0287690 | A1 | 12/2006 | Bouchataoui et al. |
| 2010/0310084 | A1* | 12/2010 | Hersbach ............. H04R 25/453 381/71.6 |
| 2011/0029031 | A1 | 2/2011 | Parker |
| 2011/0066210 | A1 | 3/2011 | Wilson |

(Continued)

*Primary Examiner* — Amir Etesam
(74) *Attorney, Agent, or Firm* — Edell, Shapiro & Finnan, LLC

(57) ABSTRACT

An audio processing pipeline, for an auditory prosthesis, includes: a common stage, including a common frequency analysis filter bank, configured to generate a common set of processed signals based on an input audio signal; and first and second stimulator-specific stages, responsive to the common set of signals and including first and second frequency-analysis filter banks, configured to generate first and second sets of processed signals adapted for the first and second hearing stimulators, respectively.

28 Claims, 13 Drawing Sheets

(56) References Cited

U.S. PATENT DOCUMENTS

2011/0178363 A1    7/2011   Van Herck et al.
2011/0264155 A1   10/2011   Van den Heuvel et al.
2012/0239385 A1    9/2012   Hersbach et al.
2013/0223635 A1    8/2013   Singer et al.

\* cited by examiner

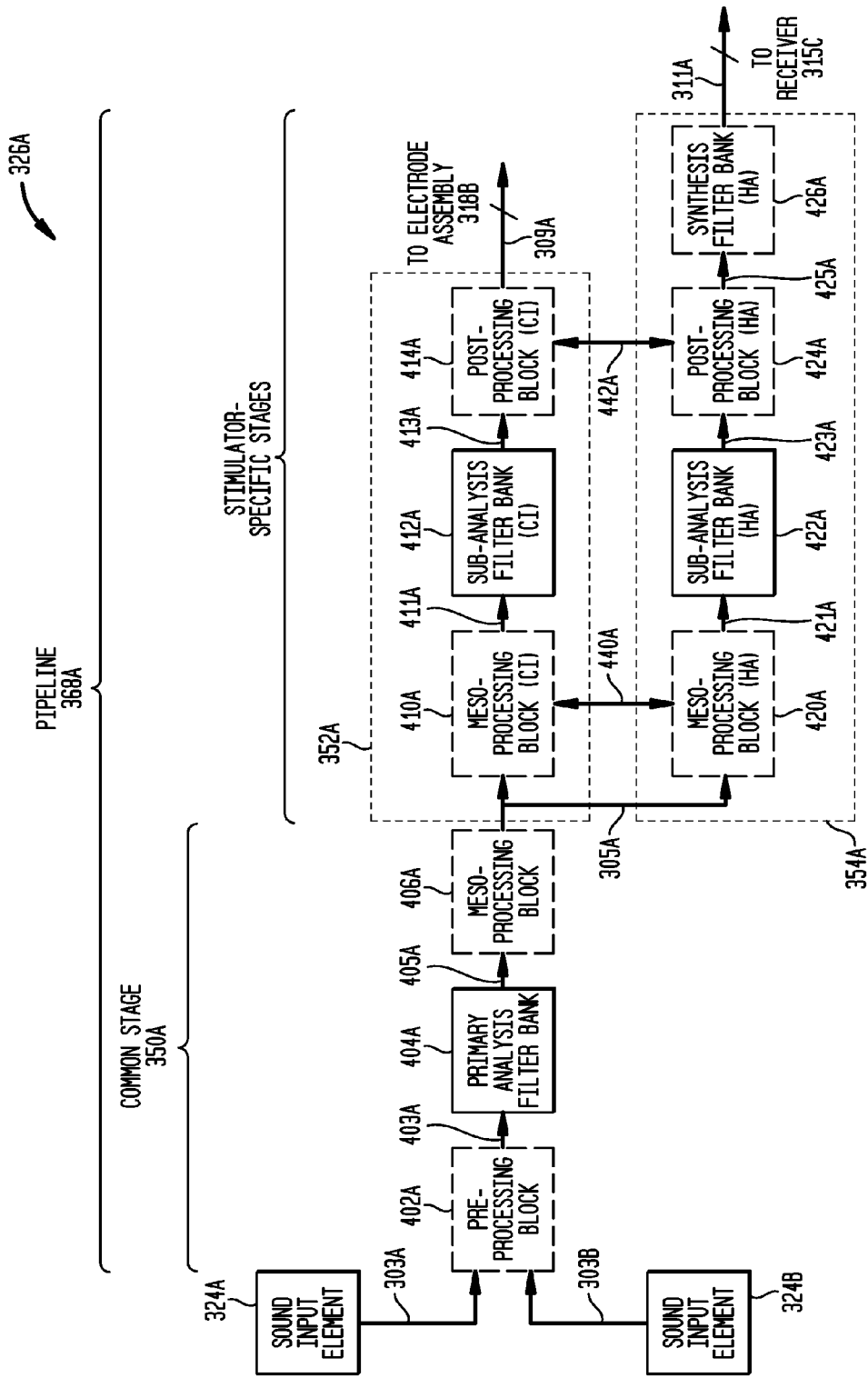

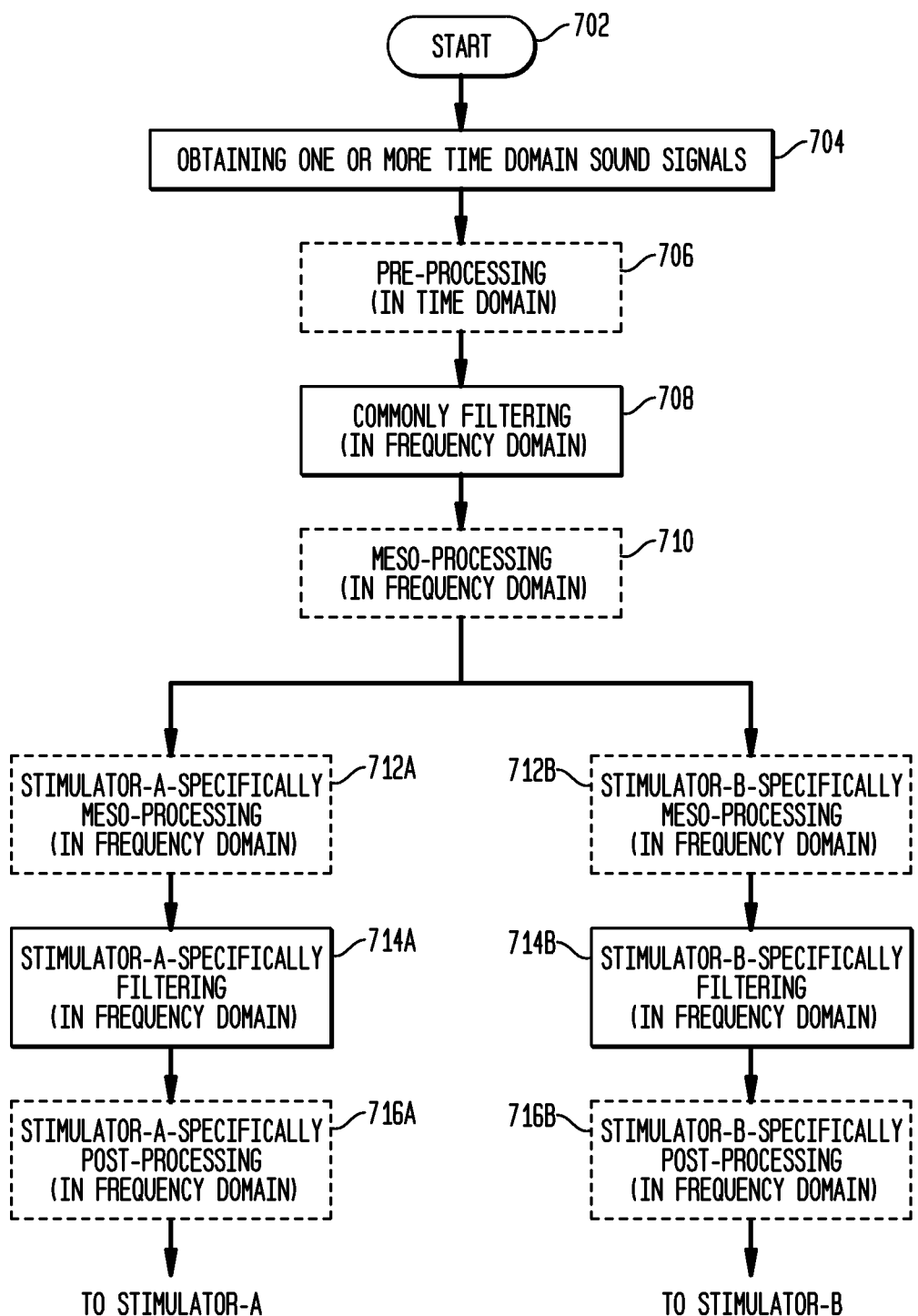

AUDIO PROCESSING PIPELINE FOR AUDITORY PROSTHESIS HAVING A COMMON, AND TWO OR MORE STIMULATOR-SPECIFIC, FREQUENCY-ANALYSIS STAGES

CROSS-REFERENCE TO RELATED APPLICATIONS

The present application is a continuation of U.S. patent application Ser. No. 14/524,377, filed on Oct. 27, 2014, which in turn is a continuation of U.S. patent application Ser. No. 13/649,494, filed on Oct. 12, 2012, now U.S. Pat. No. 8,873,770, the entire contents of which are hereby incorporated by reference.

BACKGROUND

Field of the Invention

The present technology relates generally to auditory prostheses and, more particularly, to such prostheses having a common, and two or more stimulator-specific, frequency-analysis stages.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals suffering from conductive hearing loss typically receive an auditory prosthesis that provides acoustic stimulation, e.g., an acoustic hearing aid. Hearing aids rely on principles of air conduction to transmit acoustic signals to the cochlea. Typically, a hearing aid is positioned in the ear canal or on the outer ear to amplify received sound. This amplified sound is delivered to the cochlea through the normal middle ear mechanisms resulting in the increased perception of sound by the recipient. It is worth noting that hearing aids are commonly referred to as hearing instruments by the industry and the electro-acoustic transducer (commonly referred to as the receiver) is a speaker that outputs sound to the recipient, i.e., the receiver is not the microphone.

Individuals who suffer from conductive hearing loss typically have some form of residual hearing because the hair cells in the cochlea are undamaged. As a result, individuals suffering from conductive hearing loss might receive an auditory prosthesis that provides mechanical stimulation, e.g., generates mechanical motion of the cochlea fluid. Such prostheses include, for example, bone conduction devices and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from an auditory prosthesis that provides electrical stimulation, e.g., that stimulates nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem implants might also be proposed when a recipient experiences sensorineural hearing loss if the auditory nerve, which sends signals from the cochlear to the brain, is severed or not functional.

More recently, there has been an increased interest in auditory prostheses that arecapable of using multiple types of stimulation to stimulate the recipient and thereby evoke a hearing percept. Using multiple types of stimulation provides a recipient with the ability to perceive a wider range of frequencies regardless of the cause of hearing loss. Example combinations of stimulation types in such auditory prostheses include (1) electrical stimulation and acoustic stimulation, (2) bone-conductive mechanical stimulation and middle-ear mechanical stimulation, (3) bone-conductive mechanical stimulation and acoustic stimulation, (4) electrical stimulation and middle-ear mechanical stimulation, etc.

SUMMARY

In one aspect of the present technology, an audio processing pipeline for an auditory prosthesis. The audio processing pipeline comprises: a common stage, including a common frequency analysis filter bank, configured to generate a common set of processed signals based on an input audio signal; and first and second stimulator-specific stages, responsive to the common set of signals and including first and second frequency-analysis filter banks, configured to generate first and second sets of processed signals adapted for the first and second hearing stimulators, respectively.

In another aspect of the present technology, an auditory prosthesis is provided. The auditory prosthesis comprises: a source to provide a time-domain audio signal; a sound processor responsive to the time-domain audio signal and configured to include: a common stage, including a common frequency analysis filter bank, configured to generate a common set of processed signals based on an input audio signal; and first and second stimulator-specific stages, responsive to the common set of signals and including first and second frequency-analysis filter banks, configured to generate first and second sets of processed signals adapted for different second hearing stimulators, respectively; and first and second hearing stimulators of different types responsive to the first and second sets of processed signals, respectively.

In yet another aspect of the present technology, a method of processing an audio signal is provided. The method comprises: commonly filtering, in the frequency domain, an input audio signal to generate a common set of processed signals; and stimulator-specifically filtering, in the frequency domain, the common set of signals to generate first and second sets of processed signals adapted for the first and second hearing stimulators, respectively.

BRIEF DESCRIPTION OF THE DRAWINGS

Embodiments of the present technology are described below with reference to the attached drawings, in which:

FIG. 2B is a functional block diagram of the audio-processing pipeline of FIG. 2A, in accordance with some embodiments of the present technology;

FIG. 7 is a flowchart illustrating a method of processing an audio signal, in accordance with some embodiments of the present technology, the method being adapted for a hybrid auditory prosthesis that is provided at least two hearing stimulators of different types.

DETAILED DESCRIPTION

Aspects of the present technology are generally directed to an audio processing pipeline for a hybrid auditory prosthesis having at least first and second hearing stimulators of different types. Such a pipeline comprises: a common stage, including a common frequency analysis filter bank, that is configured to generate a common set of processed signals based on an input audio signal; and first and second stimulator-specific stages, including first and second frequency-analysis filter banks, that are configured to generate first and second sets of processed signals adapted for first and second hearing stimulators, respectively. An aspect of the present technology includes the recognition that conventional hybrid auditory prostheses having two discrete processing pipelines serving stimulators of different types often have counterpart stages that perform the same operations with the same operating parameters, i.e., redundant stages. By taking a modular approach to reform the signal-processing architecture in a hybrid auditory prosthesis, redundant operations can be eliminated in favor of a common stage that feeds at least first and second stimulator-specific stages. Values for operational parameters of the common stage are based in part on values for operational parameters of the first and second stimulator-specific stages so as to avoid aliasing in the signals output therefrom relative to the common set of signals output from the common stage, respectively. Eliminating redundant stages yields benefits including reduced consumption of computational power and thereby a reduced footprint for the processor circuitry that performs such operations, easier modifications to the processing pipeline, etc.

Aspects of the present technology include pipelines which have stages, with such stages including frequency-analysis filter banks. A frequency-analysis filter bank, as used herein, refers to a device which separates an input signal into multiple sub-bands (also known as channels) that together represent at least some, if not all, of the spectrum of the input signal, i.e., which divides the input signal into a set of analysis signals, each analysis signal corresponding to a different region in the spectrum of the input signal. The process of decomposition performed by a frequency-analysis filter bank is called analysis (in the sense of analyzing the input signal in terms of its components in each sub-band). Typically, within a given frequency-analysis filter bank, the sub-bands (channels) do not overlap, and may substantially align, e.g., neighboring sub-band (channel) edges may be substantially contiguous. A frequency-analysis filter bank may be implemented, e.g., using a set of analog or digital bandpass filters that collectively provide the set of analysis signals. Various possible implementations of a frequency-analysis filter bank are discussed below.

Figure 1:
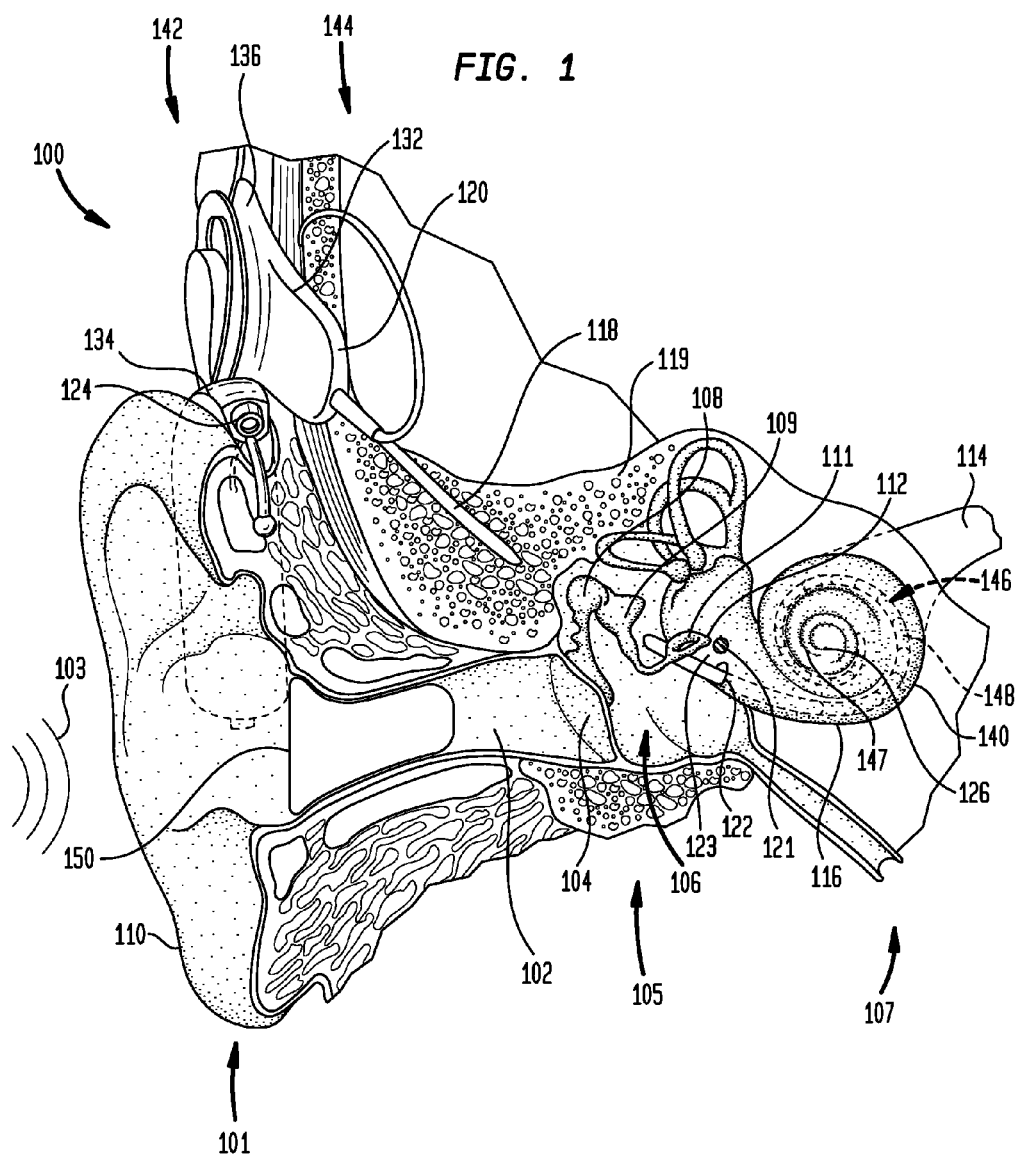
FIG. 1 is a perspective view of a hybrid auditory prosthesis, in which some embodiments of the present technology may be implemented.

FIG. 1 is a perspective view of a hybrid auditory prosthesis 100, in which some embodiments of the present technology may be implemented. More particularly, FIG. 1 is perspective view of a hybrid auditory prosthesis 100 implanted in a recipient. Prosthesis 100 implements electrical and acoustic modes of stimulation.

The recipient has an outer ear 101, a middle ear 105 and an inner ear 107. Components of outer ear 101, middle ear 105 and inner ear 107 are described below, followed by a description of auditory prosthesis 100. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising bones known as the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, auditory prosthesis 100 comprises an external component 142 which is directly or indirectly attached to the body of the recipient, and an internal or implantable stimulation module 144 which is temporarily or permanently implanted in the recipient. External component 142 can comprise one or more functional components which generate and receive data. In FIG. 1, external component 142 comprises a behind-the-ear (BTE) unit 134 having one or more sound input elements 124 for detecting sound. It would be appreciated that sound input elements 124 can comprise, for example, a microphone or an electrical input configured to connect prosthesis 100 to external equipment and receive an electrical sound signal directly there from. For example, an electrical input can permit prosthesis to be connected to, FM hearing systems, MP3 players, televisions, mobile phones, etc. For ease of illustration, embodiments of the present technology will be described herein with reference to a microphone as the sound input element.

Microphone 124 converts the detected sound into electrical signals. Disposed in BTE unit 134 is a sound processing unit (not shown) that converts the microphone output electrical signals into different frequency components of the detected sound. As described in detail below, BTE 134 can comprise a transceiver unit which transmits these electrical signals to one or more other components.

In FIG. 1, BTE unit 134 wirelessly transmits the electrical signals output by the sound processing unit to an internal transceiver unit 132 in internal component 144. Transceiver unit 132 can be positioned in a recess of the temporal bone adjacent auricle 110 of the recipient. Transceiver unit 132 transcutaneously receives power and data signals from external component 142 using one or more types of wireless transmission. For example, in certain embodiments of the present technology, radio frequency (RF) links can be used to transmit power and data to transceiver unit 132. In such embodiments, transceiver unit 132 comprises an internal coil 136, a magnet (also not shown) fixed relative to the internal coil. Internal coil 136 is typically a wire antenna coil comprised of multiple turns of electrically insulated single-strand or multi-strand platinum or gold wire. As would be appreciated, transceiver unit 132 can also transmit data signals to external component 142. For example, data signals transmitted by transceiver unit 132 can be received by the transceiver unit in BTE 134.

Implantable stimulation module 144 further comprises a power source (not shown) for storing power delivered from external component 142, a stimulator unit 120 and an elongate electrode assembly 118. Internal transceiver unit 132 and stimulator unit 120 are hermetically sealed within a biocompatible housing, sometimes collectively referred to as a main module 120. Elongate electrode assembly 118 has a proximal end connected to main module 120, and a distal end implanted in cochlea 140. Electrode assembly 118 extends from main module 120 to cochlea 140 through mastoid bone 119. Electrode assembly 118 is inserted or implanted into cochlea 140. In some embodiments of the present technology, electrode assembly 118 can be implanted at least in basal region 116, and sometimes further. For example, electrode assembly 118 can extend towards apical end 126 of cochlea 140, referred to as cochlea apex 126. In certain circumstances, electrode assembly 118 can be inserted into cochlea 140 via a cochleostomy 122. In other circumstances, a cochleostomy can be formed through round window 121, oval window 112, promontory 123 or through an apical turn 147 of cochlea 140. In certain embodiments of the present technology, an additional electrode assembly can be provided. This electrode assembly can be mounted within, or external to, the cochlea of the recipient.

As is known, electrode assembly 118 can be implanted in cochlea 140 without damaging the recipient's residual hearing. That is, implantation of electrode assembly 118 into cochlea 140 does not significantly damage the remaining hair cell population, nor does it interfere with the cochlea fluid mechanics.

Electrode assembly 118 comprises a longitudinally aligned and distally extending array 146 of electrodes 148, sometimes referred to as electrode array 146 herein, disposed along a length thereof. Although electrode array 146 can be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals based on data signals received from BTE 134, which are applied by electrodes 148 to cochlea 140, thereby stimulating auditory nerve 114 and evoking a hearing percept. Stimulator 120 and electrode assembly 118 collectively comprise an implantable stimulation module.

In FIG. 1, auditory prosthesis further comprises an external stimulation module 150 that is non-surgically positioned within the externally accessible portion of the recipient's ear. In certain embodiments of the present technology, external stimulation module 150 can comprise an in-the-ear (ITE) unit that fits within the ear bowl. Certain such devices are sometimes referred to as full shell or half shell devices. In alternative embodiments of the present technology, external stimulation module 150 can comprise a completely-in-canal (CIC) unit that is shaped to fit into the recipient's ear canal such that the unit contacts the bony portion of the ear canal. In another embodiment, external stimulation module 150 can comprise an in-the-canal (ITC) unit that is positionable just outside the ear canal. In yet another embodiment, ITE unit 150 can comprise a micro-canal (MIC) unit that is slightly smaller in size than the ITC unit.

As detailed below, external stimulation module 150 comprises a receiving unit (not shown) that wirelessly receives electrical signals representing some of the different frequency components of the detected sound signal. External stimulation module 150 also includes a receiver (also not shown) that stimulates the recipient's ear based on the received electrical signals. Thus, the receiver evokes a hearing percept of a frequency range of the detected sound. In FIG. 1, the receiver provides acoustic stimulation signals (sound waves) to the tympanic membrane 104 which vibrates in response to the acoustic stimulation signals. This vibration is coupled to the inner ear fluid via the bones of middle ear 105, thereby activating the cochlea hair cells.

As noted above, hybrid auditory prosthesis 100 delivers acoustic and electrical stimulation signals to the recipient's ear. In certain embodiments of the present technology, the acoustic and electrical stimulation signals are each delivered to cause perception of different frequency ranges of the detected sound. For example, it is known that the cochlea is tonotopically mapped. That is, certain regions of the cochlea, namely basal region 116, is responsive to high frequency signals while regions of the cochlea approaching apex 126 are responsive to increasingly lower frequency signals. Therefore, in such embodiments, electrode assembly 118 delivers electrical signals to basal region 116 to cause the recipient to perceive high frequency signals, while external stimulation module 150 delivers acoustic signals that evoke perception of lower frequency sounds.

In FIG. 1, auditory prosthesis 100 comprises external component 142 which includes BTE 134. It should be appreciated that in alternative embodiments of the present technology, external component 142 can comprise a body worn unit, a pinna attached unit, etc., instead or, or in addition to, BTE 134. In further embodiments of the present technology, external component 142 can be fully or partially omitted. In such embodiments, implantable stimulation module 144 is capable of operating, at least for a period of time, without the need for an external device.

For example, some embodiments of the present system can beneficially comprise an external stimulation module 150 in which a receiver (not illustrated) does not occlude ear canal 102. Unlike traditional hearing aids or other systems using an acoustic output component, stimulation for high frequency sound components are generated and delivered by a non-acoustic amplification module, thus avoiding acoustic feedback which have been problematic with certain past systems. Instead, according to some embodiments of the present technology, high-frequency sound components can be directed to the basilar region of cochlea 140, while only low-frequency sound components will be emitted by external stimulation module 150, thus avoiding feedback of high-frequency sound components. It is to be understood that external stimulation module 150 can be formed and configured to occlude ear canal 102, or can be made (for example, as a cylinder having a hollow center) so as to allow the passing of air, sound, moisture, etc. through external stimulation module 150.

As noted, implantable stimulation module 144 further comprises a power source (not shown) that stores power received from an external device. The power source can comprise, for example, a rechargeable battery. During operation of implantable stimulation module 144, the power stored by the power source is distributed to the various other implanted components as needed. The power source can be located in the main module 120, or disposed in a separate implanted location.

Figure 2A:
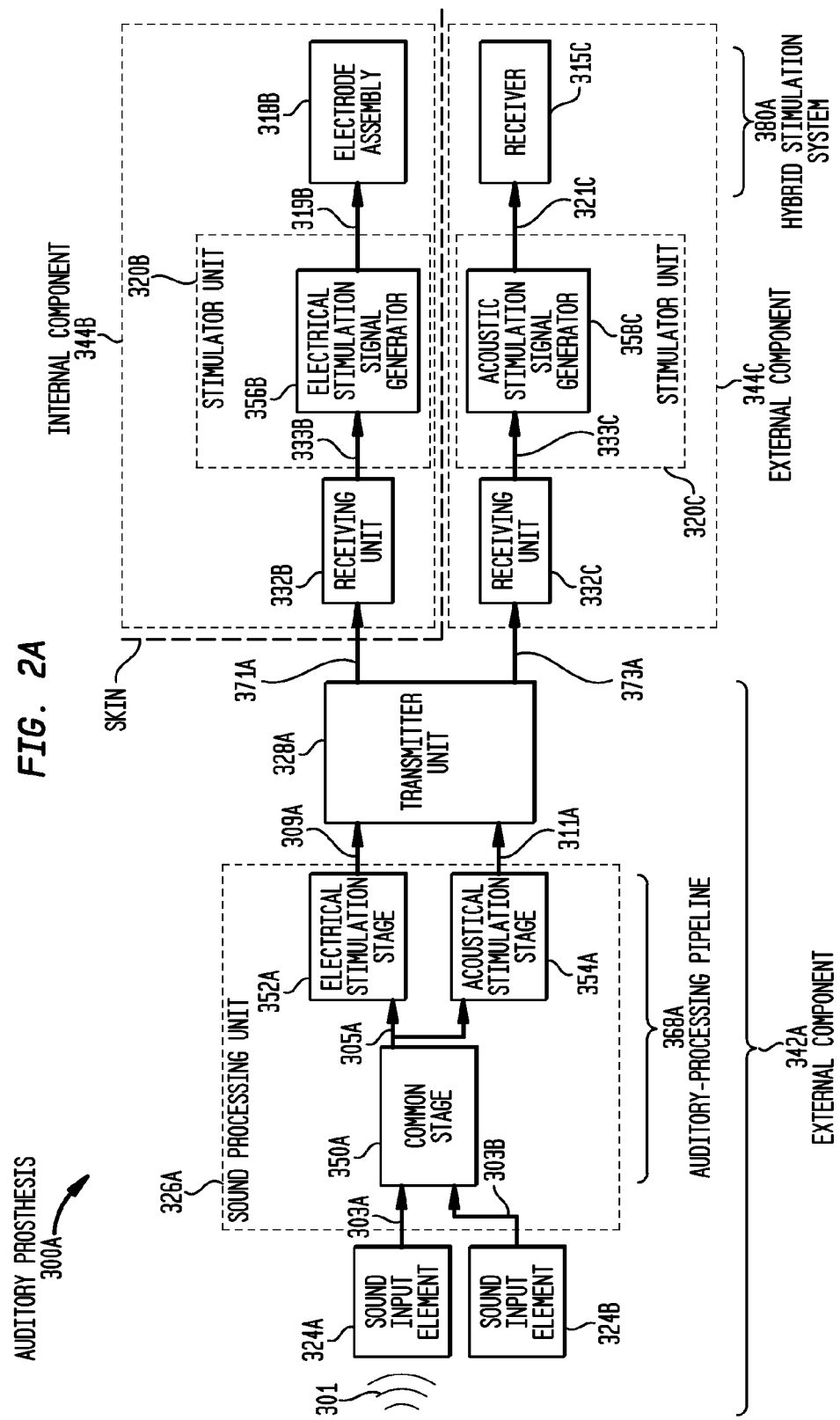
FIG. 2A is a functional block diagram illustrating the hybrid auditory prosthesis of FIG. 1 as being provided with an audio-processing pipeline having a common stage and two or more stimulator-specific frequency-analysis stages, in accordance with some embodiments of the present technology.

FIG. 2A is a functional block diagram illustrating hybrid auditory prosthesis 100 of FIG. 1 (referred to as hybrid auditory prosthesis 300A in FIG. 2A) as being provided with an audio processing signal-path architecture, referred to herein as an audio-processing pipeline 368A, having a common stage 350A and two or more stimulator-specific frequency-analysis stages 352A and 354A, in accordance with some embodiments of the present technology.

In FIG. 2A, hybrid auditory prosthesis 300A comprises an external component 342A, an internal component 344B and an external component 344C. External component 342A comprises one or more sound input elements 322A, 324B, etc., for detecting sound, a sound processing unit 326A (having pipeline 368A), a power source (not shown) and an external transmitter unit 328A. Each of sound input elements 324A, 324B, etc., can be a microphone, telephone coil (t-coil), a wireless signal-format receiving device, e.g., an FM-receiving device, a memory storing a digitized version of a time-domain signal, etc. Sound input elements 324A, 324B, etc., can be the same or different.

One or more of sound input elements 322A, 324B, etc., can receive a sound wave 301 and generates one or more electrical signals 303A, 303B, etc., representing the sound. Electrical signals 303A, 303B, etc., are provided to sound processing unit 326A which converts the signal(s) into encoded data signals which can be transmitted to internal component 344B.

More particularly, in FIG. 2A, one or more of electrical signals 303A, 303B, etc., is provided to a common stage 350A. In some embodiments of the present technology, common stage 350A filters (in the frequency-domain) and processes one or more of electrical signals 303A, 303B, etc., in a manner appropriate to the needs of the two or more different types of stimulation to be generated (as will be discussed in more detail below) and provides a common set of signals 305A to stimulator-specific stages, e.g., an electrical stimulation stage 352A and an acoustical stimulation stage 354A.

While illustrated as separate blocks in FIG. 2A, common stage 350A, electrical stimulation stage 352A and an acoustical stimulation stage 354A need not necessarily be physically separate implementations. Rather, for example, a single processor could physically implement the respective stages, treating them as discrete processing operations.

Electrical stimulation stage 352A further filters (in the frequency domain) and processes common signal set 305A to generate a first set 309A of processed signals adapted for electrode assembly 118 (which is referred to in FIG. 2A as electrode assembly 318B), e.g., wherein first signal set 309A corresponds to a high frequency portion of the audible frequency spectrum, which, as described above, is perceivable by basal region 116 of cochlea 140. Acoustical stimulation stage 354A further filters (in the frequency domain) and processes common signal set 305A to generate a second set 311A of processed signals adapted for receiver 315C, e.g., wherein second signal set 311A corresponds to a low frequency portion of the audible frequency spectrum. It is noted that first signal set 309A is NOT adapted for receiver 315C, and that second signal set 311A is NOT adapted for electrode assembly 318B.

Signals 309A and 311A are provided to transmitter unit 328A where the signals are encoded and are then transmitted, e.g., as RF signals 371A and 373A, to receiving units 332B and 332C in internal component 344B and external component 344C, respectively. Receiving units 332B and 332C decode the transmitted signals, and provide electrical signals 333B and 333C to stimulator units 320B and 320C, respectively.

Based on electrical signals 333B and 333C, stimulator units 320B and 320C generate stimulation signals which are provided to one or more components of hybrid stimulation system 380A. As shown, hybrid stimulation system 380A comprises an electrode assembly 318B and receiver 315C. Stimulator unit 320B comprises electrical stimulation signal generator 356B configured to generate electrical stimulation signals 319B based on electrical signals 333B. Electrical stimulation signals 319B are provided to electrode assembly 318B for delivery to the recipient, thereby stimulating auditory nerve 114. Stimulator unit 320C comprises an acoustic stimulation signal generator 358C configured to generate acoustic stimulation signals 321C based on electrical signals 333C. Acoustic stimulation signals 321C are provided to receiver 315C for delivery to the recipient, thereby also stimulating auditory nerve 114.

Although FIG. 2A has been described with reference to hybrid auditory prosthesis 300A having external component 342A, in alternative embodiments of the present technology, it should be appreciated that component 342A can be implantable as well, e.g., integrated with internal component 344B. In such embodiments, sound processing unit 326A can be implanted in a recipient, e.g., in mastoid bone 119, such that sound processing unit 326A can communicate directly with stimulator unit 320B, thereby eliminating the portion of transmitter unit 328A that is provided for communication with receiving unit 332B, and eliminating receiving unit 332B as well. Similarly, external component 344C could be incorporated within external component 342A, thereby eliminating the portion of transmitter unit 328A that is provided for communication with receiving unit 332C, and eliminating receiving unit 332C as well.

FIG. 2B is a functional block diagram of audio-processing pipeline 368A included in sound processing unit 326A of hybrid auditory prosthesis 300A of FIG. 2A, in accordance with some embodiments of the present technology. Pipeline 368A includes common stage 350A and two stimulator-specific frequency-analysis stages 352A and 354A. Alternatively, additional stimulator-specific stages (not illustrated in FIG. 2B) can be provided in correspondence to additional types of stimulation (not illustrated in FIG. 2B) that may be provided.

In FIG. 2B, common stage 350A is illustrated as including a primary analysis filter bank 404A, and an optional pre-processing block 402A and an optional meso-processing block 406A. Values for operational parameters of common stage 350A, in particular, pre-processing block 402A, primary analysis filter bank 404A and meso-processing block 406A, are based in part upon values for operational parameters used by electrical stimulation stage 352A and acoustical stimulation stage 354A so as to avoid aliasing in first signal set 309A and second signal set 311A, respectively.

Pre-processing block 402A performs processing operations, e.g., time-domain multi-microphone processing (e.g., Zoom and Beam), that may be advantageous to perform in the time-domain, e.g., at least at a location along pipeline 368A before a signal representing sound wave 301 reaches primary analysis filter bank 404A. Other examples of pre-processing operations that can be performed by pre-processing block 402A include various types of broadband compression, dynamic range expansion, amplitude scaling (limiting/reducing or gaining), etc. Pre-processing block 402A outputs signals 403A to primary analysis filter bank 404A. For example, internally and after performing the time-domain processing, pre-processing block 402A can transform the signals being processed (e.g., signals 303A and 303B) into the frequency domain such that output signal 403A is already a frequency-domain signal.

Primary analysis filter bank 404A is configured to perform a frequency-analysis type of filtering that has both sufficient resolution in the frequency-domain and a sufficient update/analysis rate so that its output signals 405A are suitable for use in all further processing, e.g., such that common signal set 305A (which is dependent on signals 405A) will be sufficient to avoid aliasing in first signal set 309A and second signal set 311A, respectively. Values for operational parameters of primary analysis filter bank 404A should be chosen with the specific hearing instrument outputs in mind, here (in the context of FIGS. 1, 2A and 2B) electrode assembly 318B and receiver 315C.

For example, primary analysis filter bank 404A can be configured with a Fast Fourier Transform (FFT) device that operates upon a 128 point window (also referred to as a 128 input sample window) using a 16 kHz sampling rate, with successive windows overlapping every 8 points/input samples (resulting in 65 linear channels spaced 125 Hz apart), and using an update rate of 1000 Hz.

Figure 2C:
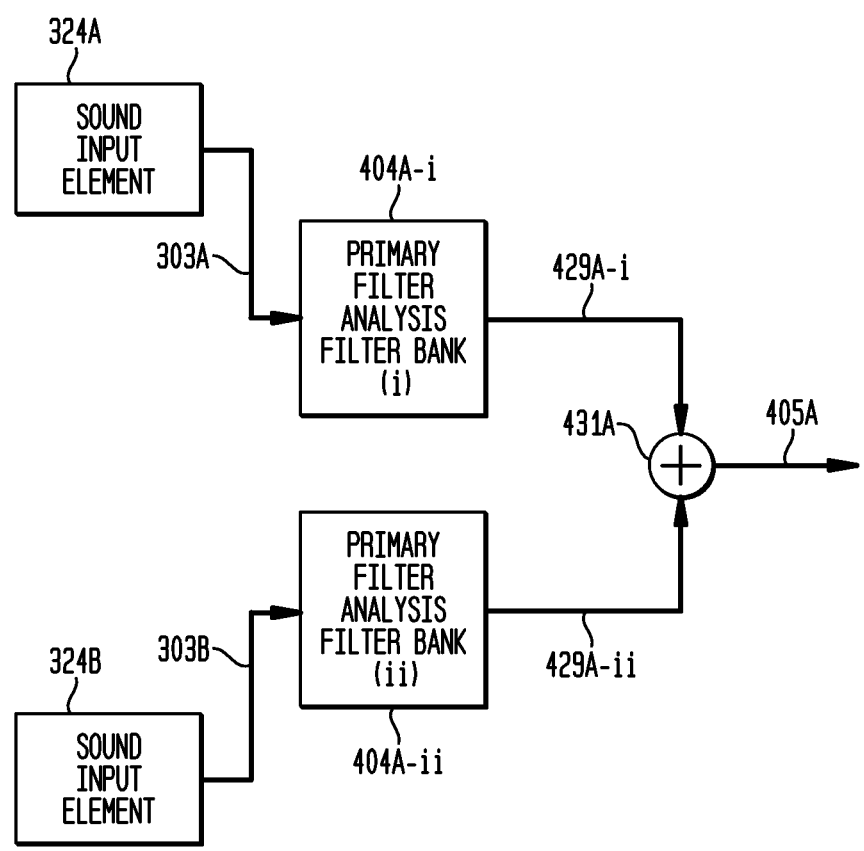
FIG. 2C is a functional block diagram of an alternative front end arrangement of the common stage of FIG. 2B, in accordance with some embodiments of the present technology.

FIG. 2C is a functional block diagram of an alternative front end arrangement of common stage 350A of FIG. 2B, in accordance with some embodiments of the present technology. In FIG. 2C (relative to FIG. 2B), pre-processing block 402A has been eliminated, a second instance of primary analysis filter bank 404A has been added (resulting in filter banks 404A-i and 404A-ii) and a signal summation block 431A has been added. Signals 303A and 303B are provided to primary analysis filter bank 404A-i and primary analysis filter bank 404A-ii, respectively. Primary analysis filter banks 404A-i and 404A-ii are each configured to perform a frequency-analysis type of filtering that has both sufficient resolution in the frequency-domain and a sufficient update/analysis rate so that their output signals 429A-i and 429A-ii are suitable for use in all further processing. Signals 429A-i and 429A-ii are provided to, and combined at, block 431A, resulting in signals 405A. As discussed above, output signals 405A are suitable for use in all further processing, e.g., such that common signal set 305A (which is dependent on signals 405A) will be sufficient to avoid aliasing in first signal set 309A and second signal set 311A, respectively.

Returning to FIG. 4B, meso-processing block 406A can perform operations that are advantageously done in the frequency-domain (e.g., so as to operate on signals 405A as output by primary analysis filter bank 404A). Examples of operations that can be performed by meso-processing block 406A include various types of multi-channel compression, dynamic range expansion, noise reduction and/or amplitude scaling. The output of meso-processing block 406A is common signal set 305A. In the absence of optional meso-processing block 406A, common signal set 305A is the output of primary analysis filter bank 404A, i.e., is signals 405A.

As to the stimulator-specific stages of FIG. 2B, each of electrical stimulation stage 352A and acoustical stimulation stage 354A includes corresponding sub-analysis filter banks 412A and 422A, optional corresponding meso-processing blocks 410A and 420A and optional corresponding post-processing blocks 414A and 424A, respectively. Meso-processing blocks 410A and 420A output signals 411A and 421A to sub-analysis filter banks 412A and 422A, respectively. Sub-analysis filter banks 412A and 422A output signals 413A and 423A to post-processing blocks 414A and 424A, respectively.

According to some embodiments of the present technology, the same operations are performed in corresponding meso-processing blocks 410A and 420A, sub-analysis filter banks 412A and 422A, and post-processing blocks 414A and 424A, albeit with different values of operational parameters thereof in order to reflect the different stimulators to which stimulator-specific stages 352A and 354A adapt signals, namely electrode assembly 318B and receiver 315C, respectively. For example, the Adaptive Dynamic Range Optimization (ADRO®) type of automatic gain control, multi-channel noise reduction and/or frame/sampling rate conversions can be performed by meso-processing blocks 410A and 420A albeit using different values of operating parameters in order to adapt the processed signals to electrode assembly 318B and receiver 315C, respectively. For example (and continuing the example begun above), electrical stimulation stage 352A can convert from the 1000 Hz update rate of primary analysis filter bank 404A to an update rate of 2400 Hz in order to support a rate of 2400 pulses/stimuli per second (pps) per electrode, while acoustical stimulation stage 354A can remain at the 1000 Hz update rate of primary analysis filter bank 404A. According to an alternative embodiment, at least one of corresponding meso-processing blocks 410A and 420A, sub-analysis filter banks 412A and 422A, and post-processing blocks 414A and 424A, respectively, differ in terms of at least operation performed therein.

Relative to a context in which one or more of the same operations are performed (albeit with different values of operational parameters thereof, as discussed above) (hereinafter, counterpart operations) in each of corresponding meso-processing blocks 410A and 420A and/or and in each of corresponding post-processing blocks 414A and 424A, according to other alternative embodiments of the present technology, at least one of corresponding meso-processing blocks 410A and 420A and/or and corresponding post-processing blocks 414A and 424A are configured to coordinate the timing of at least one of the counterpart operations performed therein, as indicated by two-headed arrows 440A and 442A, respectively.

Sub-analysis filter banks 412A and 422A select subsets of the frequency range bandwidth provided by primary analysis filter bank 404A, wherein such subsets are appropriate for adapting resulting signals 413A and 423A to electrode assembly 318B and receiver 315C, respectively. For example, sub-analysis filter bank 412A can output signals in a range of about 2 kHz to about 8 kHz, and sub-analysis filter bank 422A can output signals in a range of about 0 Hz to about 2 kHz. Alternatively, sub-analysis filter banks 412A and 422A can be configured so that signals 413A and 423A have overlapping albeit different (i.e., not coextensive) frequency ranges.

The number of channels at the output of each of sub-analysis filter banks 412A and 422A and the associated channel widths are the result of having made different combinations of the channels generated by primary analysis filter bank 404A, i.e., are the result of having made different combinations of the channels present in common signal set 305A. Typically such combinations represent reductions in the number of channels relative to the number of channels present in common signal set 305A. For example (and continuing the example begun above), starting with the 65 channels provided by primary analysis filter bank 404A, sub-analysis filter bank 412A can use 8 of the 65 channels below about 2 kHz, while sub-analysis filter bank 422A can use 6 of the 65 channels above about 2 kHz.

Post-processing at locations along pipeline 368A subsequent to each of sub-analysis filter banks 412A and 422A allows stimulator-specific operations to be performed. For example, post-processing block 414A can perform maxima selection and mapping of maxima-amplitude to level-of-current for each electrode in electrode assembly 318B. Also, for example, post-processing block 424A can perform compression, dynamic range expansion and/or amplitude scaling for receiver 315C.

Acoustic stimulation stage 354A optionally further includes a synthesis filter bank 426A that receives signals 425A from post-processing block 424A and outputs signals 311A. In synthesis filter bank 426A, e.g., an inverse FFT (IFFT) device can inversely transform signals 425A from the frequency domain back to the time domain in order to generate signals 311A. In the case of electrical stimulation stage 352A, a synthesis filter bank akin to synthesis filter bank 426A is not required. If synthesis filter bank 426A is not included, then signals 311A instead correspond to signals 425A.

In alternative embodiments of the present technology, primary analysis filter bank 404A, sub-analysis filter banks 412A and/or 422A and/or synthesis filter bank 426A can be configured with filter structures and related processing based on something other than FFT analysis. Other suitable filter structures and related processing can be based on Finite Impulse Response (FIR) analysis, Infinite Impulse Response (IIR) analysis, wavelet analysis, etc.

In other alternative embodiments of the present technology, pre-processing block 402A can process primarily in the frequency domain. As such, as a preliminary operation, pre-processing block 402A would transform time-domain signals 303A, 303B, etc. into the frequency domain before performing the processing mentioned above, namely one or more of broadband compression, dynamic range expansion, amplitude scaling (limiting/reducing or gaining), multi-microphone processing etc. In this embodiment, signals 403A would be in the frequency-domain already.

Figure 3:
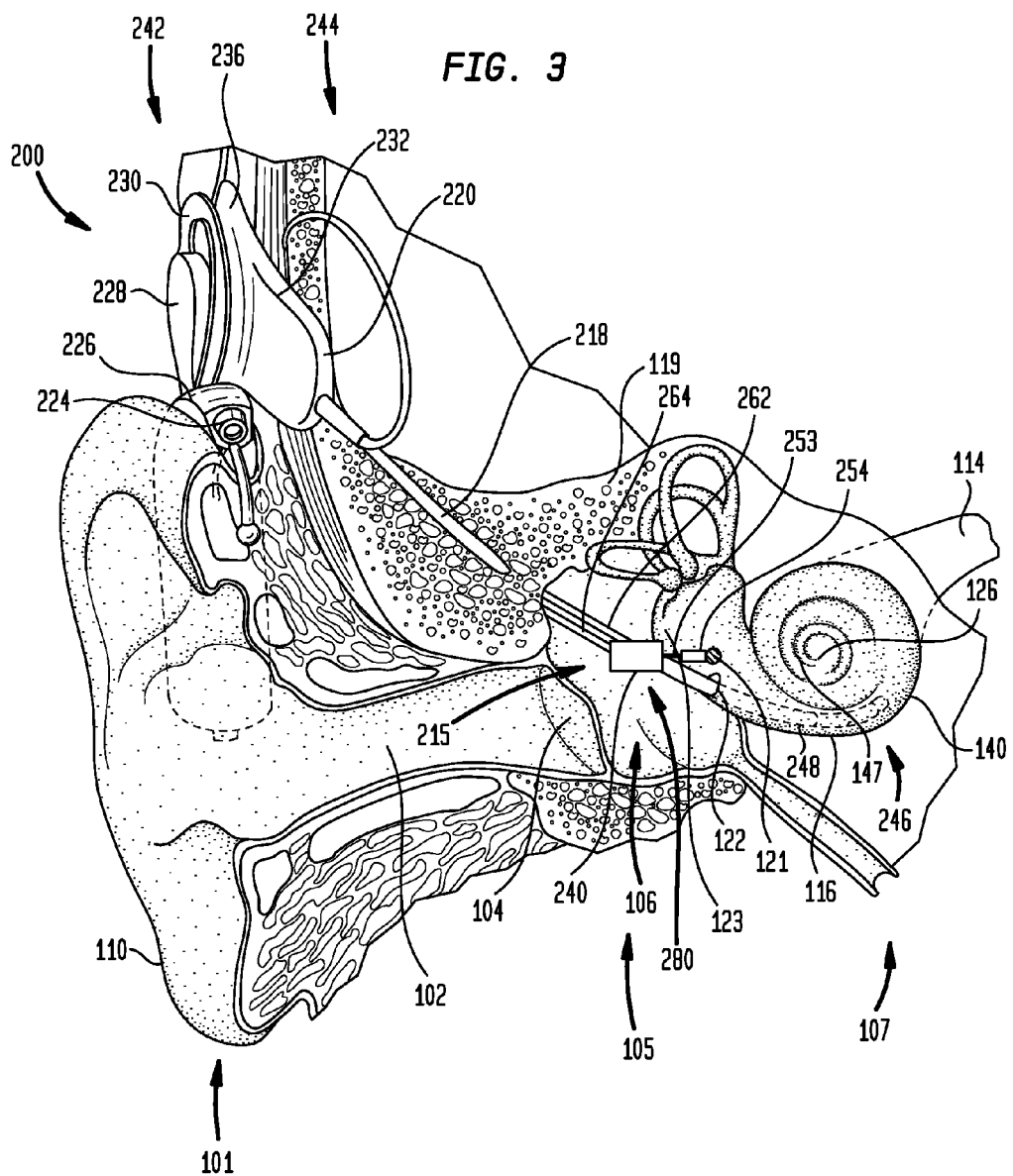
FIG. 3 is a perspective view of another hybrid auditory prosthesis, in which some embodiments of the present technology may be implemented.

FIG. 3 is a perspective view of another hybrid auditory prosthesis 200, in which some embodiments of the present technology may be implemented. Prosthesis 200 implements electrical and mechanical modes of stimulation.

In FIG. 3, hybrid auditory prosthesis 200 comprises an external component 242 which is directly or indirectly attached to the body of the recipient, and an internal component 244 which is temporarily or permanently implanted in the recipient. External component 242 typically comprises one or more sound input elements, such as microphone 224 for detecting sound, a sound processing unit 226, a power source (not shown), and an external transmitter unit 228. External transmitter unit 228 comprises an external coil 230 and, preferably, a magnet (not shown) secured directly or indirectly to external coil 230. Sound processing unit 226 processes the output of microphone 224 that is positioned, in the depicted embodiment, by auricle 110 of the recipient. Sound processing unit 226 generates encoded signals, sometimes referred to herein as encoded data signals, which are provided to external transmitter unit 228 via a cable (not shown).

Internal component 244 comprises an internal receiving unit 232, a stimulator unit 220, and a hybrid stimulation system 280. Hybrid stimulation system 280 comprises an elongate electrode assembly 218 and a mechanical stimulation arrangement 215. Internal receiving unit 232 comprises an internal coil 236, and preferably, a magnet (also not shown) fixed relative to the internal coil. Internal receiving unit 232 and stimulator unit 220 are hermetically sealed within a biocompatible housing, sometimes collectively referred to as a stimulator/receiving unit.

In FIG. 3, external coil 230 transmits electrical signals (i.e., power and stimulation data) to internal coil 236 via a radio frequency (RF) link. Internal coil 236 is typically a wire antenna coil comprised of multiple turns of electrically insulated single-strand or multi-strand platinum or gold wire. The electrical insulation of internal coil 236 is provided by a flexible silicone molding (not shown). In use, implantable receiving unit 232 can be positioned in a recess of the temporal bone adjacent auricle 110 of the recipient.

As noted, internal component 244 further includes a hybrid stimulation system 280. As shown, hybrid stimulation system 280 comprises an electrode assembly 218 which is configured to be implanted in cochlea 140. Electrode assembly 218 comprises a longitudinally aligned and distally extending array 246 of electrodes 248, sometimes referred to as electrode array 246 herein, disposed along a length thereof. Although electrode array 246 can be disposed on electrode assembly 218, in most practical applications, electrode array 246 is integrated into electrode assembly 218. As such, electrode array 246 is referred to herein as being disposed in electrode assembly 218. The proximal end of electrode assembly 218 is electrically connected to a lead 262 extending from stimulator unit 220. As described below, in some embodiments of the present technology, stimulator unit 220 generates, based on data signals received at receiving unit 232, electrical stimulation signals which are delivered to electrode assembly 218 via lead 262. The stimulation signals are applied by electrodes 248 to cochlea 140, thereby stimulating auditory nerve 114.

As described in greater detail below, electrode assembly 218 is implanted at least in basal region 116 of cochlea 140, and sometimes further. For example, electrode assembly 218 can extend towards apical end 126 of cochlea 140, referred to as cochlea apex 126. In certain circumstances, electrode assembly 218 can be inserted into cochlea 140 via a cochleostomy 122. In other circumstances, a cochleostomy can be formed through round window 121, oval window 112, the promontory 123 or through an apical turn 147 of cochlea 140.

Electrode assembly 218 can comprise a perimodiolar electrode assembly which is configured to adopt a curved configuration during and or after implantation into the recipient's cochlea. In one such embodiment, electrode assembly 218 is pre-curved to the same general curvature of a cochlea. Electrode assembly 218 is held straight by, for example, a stiffening stylet (not shown) which is removed during implantation so that the assembly adopts the curved configuration. Other methods of implantation, as well as other electrode assemblies which adopt a curved configuration may be used in alternative embodiments of the present technology.

In other embodiments of the present technology, electrode assembly 218 comprises a non-perimodiolar electrode assembly which does not adopt a curved configuration. For example, electrode assembly 218 can comprise a straight assembly or a mid-scala assembly which assumes a mid-scala position during or following implantation.

As shown in FIG. 3, hybrid stimulation system 280 further comprises mechanical stimulation arrangement 215. As previously noted, a mechanical stimulation arrangement in accordance with some embodiments of the present technology can comprise a middle ear or inner ear mechanical stimulator, or a bone conduction device. Details of exemplary bone conduction devices that may be utilized with embodiments of the present technology are described in published U.S. Patent Application US2005-0029031. For ease of illustration, some embodiments of the present technology will be described with reference to a mechanical stimulation arrangement that stimulates the recipient's inner ear; however, this exemplary illustration should not be considered to limit the present technology.

In the illustrative embodiment of FIG. 3, ossicles 106 have been omitted from FIG. 3 to illustrate location of the inner ear mechanical stimulation arrangement 215. It should be appreciated that stimulation arrangement 215 can be implanted without disturbing ossicles 106.

Stimulation arrangement 215 comprises an actuator 240 electrically connected to stimulator unit 220 by lead 264, a stapes prosthesis 254 and a coupling element 253. In this illustrative embodiment, coupling element 253 connects actuator 240 to stapes prosthesis 254 which abuts round window 121. In certain embodiments of the present technology, based on data signals received at receiving unit 232, stimulator unit 220 generates actuator drive signals which cause vibration of actuator 240. This vibration is transferred to the inner ear fluid (perilymph) in the recipient's scala tympani via coupling element 253 and stapes prosthesis 254, thereby evoking a hearing percept by the recipient.

Figure 4A:
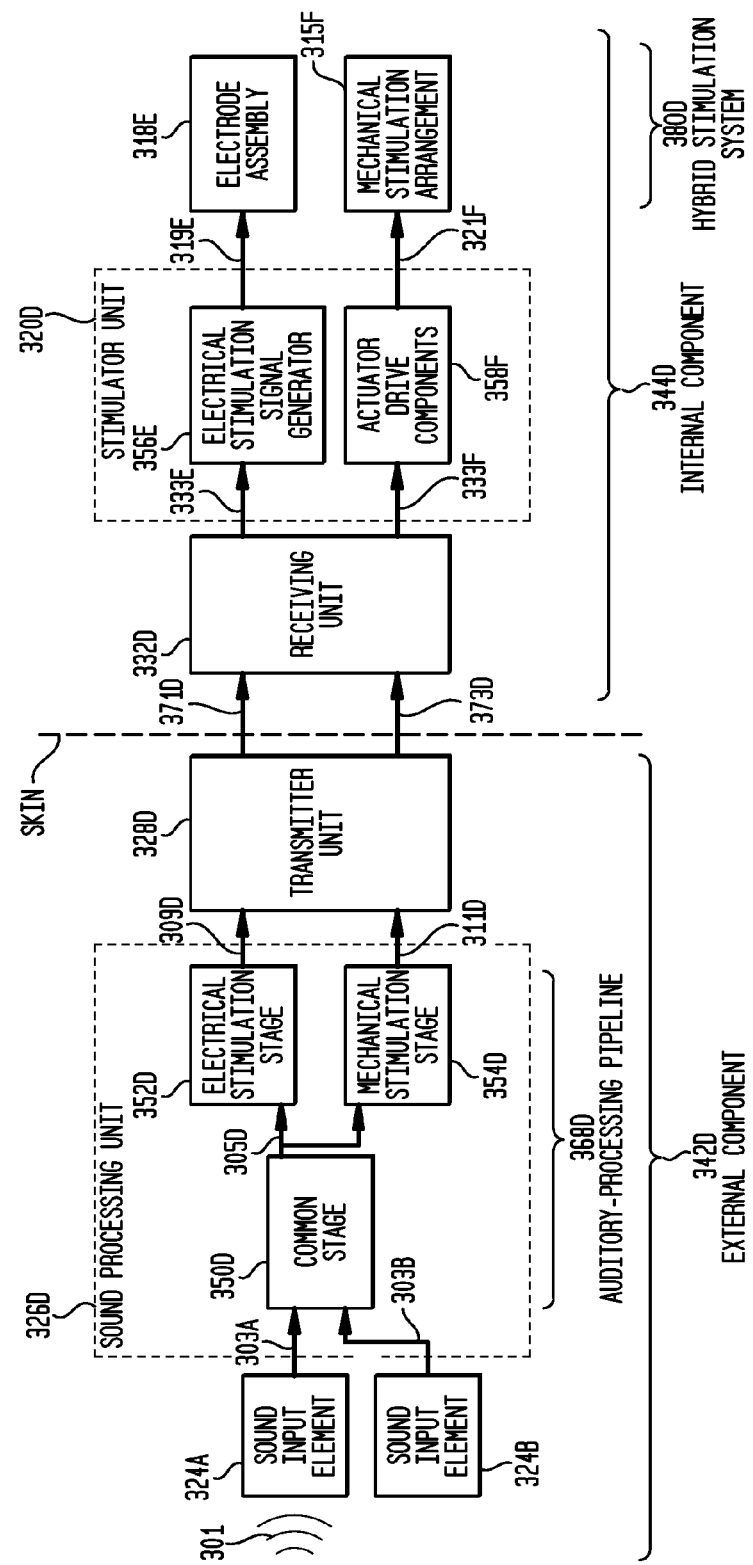
FIG. 4A is a functional block diagram illustrating the hybrid auditory prosthesis of FIG. 3 as being provided with another audio processing pipeline having a common stage and two or more stimulator-specific frequency-analysis stages, in accordance with some embodiments of the present technology.

FIG. 4A is a functional block diagram illustrating an embodiment of hybrid auditory prosthesis 200, referred to herein as hybrid auditory prosthesis 300D. In the illustrated embodiment, hybrid auditory prosthesis 300D comprises an external component 342D, and an internal component 344D. External component 342D comprises one or more sound input elements 324A, 324B, etc., for detecting sound, a sound processing unit 326D, a power source (not shown) and an external transmitter unit 328D.

One or more of sound input elements 324A, 324B, etc., receives a sound wave 301 and generates one or more electrical signals 303A, 303B, etc., representing the sound. Electrical signals 303A, 303B, etc., are provided to sound processing unit 326D which converts the signal(s) into encoded data signals which can be transmitted to internal component 344D.

More particularly, in FIG. 4A, one or more of electrical signals 303A, 303B, etc., is provided to a common stage 350D. In some embodiments of the present technology, common stage 350D performs filtering (in the frequency-domain) and processing of one or more of electrical signals 303A, 303B, etc., in a manner appropriate to the needs of the two or more different types of stimulation to be generated (as will be discussed in more detail below) and provides a common set of signals 305D to stimulator-specific stages, e.g., an electrical stimulation stage 352D and a mechanical stimulation stage 354D. Electrical stimulation stage 352D further filters (in the frequency domain) and processes common signal set 305D to generate a first set 309D of processed signals adapted for electrode assembly 318E, e.g., wherein first signal set 309D corresponds to a high frequency portion of the audible frequency spectrum, which, as described above, is perceivable by basal region 116 of cochlea 140. Mechanical stimulation stage 354D further filters (in the frequency domain) and processes common signal set 305D to generate a second set 311D of processed signals adapted for mechanical stimulation arrangement 315F, e.g., wherein second signal set 311D corresponds to a low frequency portion of the audible frequency spectrum, which is perceivable by apical regions of a cochlea. It is noted that first signal set 309D is NOT adapted for mechanical stimulation arrangement 315F, and that second signal set 311D is NOT adapted for electrode assembly 318E.

Signals 309D and 311D are provided to transmitter unit 328D where the signals are encoded and transmitted, e.g., as RF signals 371D and 373D, to receiving unit 332D in internal component 344D. Internal receiving unit 332D decodes the transmitted signals, and provides electrical signals 333E and 333F to stimulator unit 320D.

Based on electrical signals 333E and 333F, stimulator unit 320D generates stimulation signals which are provided to one or more components of hybrid stimulation system 380D. As shown, hybrid stimulation system 380D comprises an electrode assembly 318E and a mechanical stimulation arrangement 315F. Stimulator unit 320D comprises an electrical stimulation signal generator 356E configured to generate electrical stimulation signals 319E based on electrical signals 333E. Electrical stimulation signals 319E are provided to electrode assembly 318E for delivery to the recipient, thereby stimulating auditory nerve 114.

Stimulator unit 320D further comprises actuator drive components 358F. Based on signal 333F, actuator drive components 358F generate stimulation signals 321F which are provided to mechanical stimulation arrangement 315F. Stimulation signals 321F, sometimes referred to herein as actuator drive signals 321F, cause vibration of an actuator within mechanical stimulation arrangement 315F. As described above, in certain embodiments of the present technology, the actuator is coupled to the recipient's inner ear, the vibration is transferred to the inner ear fluid, thereby evoking a hearing percept by the recipient. In other embodiments of the present technology, the actuator is a positioned to deliver vibration to the recipient's skull. For example, the actuator may be part of an externally worn bone conduction device, or an implanted bone conduction device.

Although FIG. 4A with reference to hybrid auditory prosthesis 300D having external component 342D, in alternative embodiments of the present technology, it should be appreciated that hybrid auditory prosthesis can be a totally implantable device. In such embodiments, sound processing unit 326D can be implanted in a recipient in mastoid bone 119 such that sound processing unit 326D can communicate directly with stimulator unit 320D, thereby eliminating the need for transmitter unit 328D and receiving unit 332D.

Figure 4B:
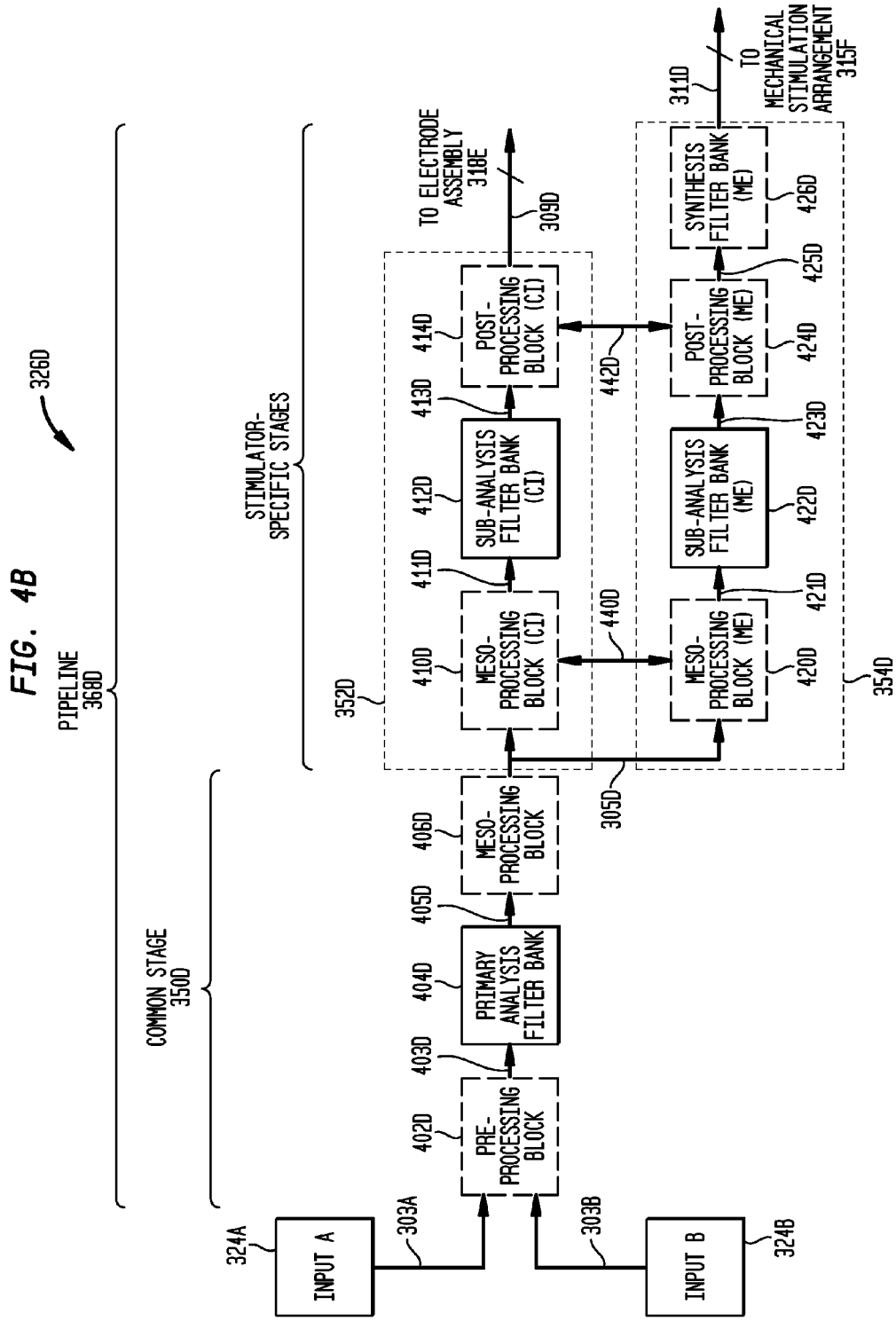
FIG. 4B is a functional block diagram of the audio-processing pipeline of FIG. 4A, in accordance with some embodiments of the present technology.

FIG. 4B is a functional block diagram of audio-processing pipeline 368D included in sound processing unit 326D of hybrid auditory prosthesis 300D of FIG. 4A, in accordance with some embodiments of the present technology. Pipeline 368D includes common stage 350D and two stimulator-specific frequency-analysis stages 352D and 354D. Alternatively, additional stimulator-specific stages (not illustrated in FIG. 4B) can be provided in correspondence to additional types of stimulation (not illustrated in FIG. 4B) that may be provided.

In FIG. 4B, common stage 350G is illustrated as including a primary analysis filter bank 404D, and an optional pre-processing block 402D and an optional meso-processing block 406D. Values for operational parameters of common stage 350D, in particular, pre-processing block 402D, primary analysis filter bank 404D and meso-processing block 406D, are based in part on values for operational parameters used by electrical stimulation stage 352D and mechanical stimulation stage 354D so as to avoid aliasing in first signal set 309D and second signal set 311D, respectively.

Pre-processing block 402D performs processing operations, e.g., time-domain multi-microphone processing (e.g., Zoom and Beam), that may be advantageous to perform in the time-domain, e.g., at least at a location along pipeline 368D before a signal representing sound wave 301 reaches primary analysis filter bank 404D. Other examples of pre-processing operations that can be performed by pre-processing block 402D include various types of broadband compression, dynamic range expansion, amplitude scaling (limiting/reducing or gaining), etc. Pre-processing block 402D outputs signals 403D to primary analysis filter bank 404D. For example, internally and after performing the time-domain processing, pre-processing block 402D can transform the signals being processed (e.g., signals 303A and 303B) into the frequency domain such that output signal 403D is a frequency-domain signal.

Primary analysis filter bank 404D is configured to perform a frequency-analysis type of filtering that has both sufficient resolution in the frequency-domain and a sufficient update/analysis rate so that its output signals 405D are suitable for use in all further processing, e.g., such that common signal set 305D (which is dependent on signals 405D) will be sufficient to avoid aliasing in first signal set 309D and second signal set 311D, respectively. Values for operational parameters of primary analysis filter bank 404D should be chosen with the specific hearing instrument outputs in mind, here (in the context of FIGS. 3, 4A and 4B) electrode assembly 318E and mechanical stimulation arrangement 315F.

For example, primary analysis filter bank 404D can be configured with a Fast Fourier Transform (FFT) device that operates on a 128 point window (also referred to as a 128 input sample window) using a 16 kHz sampling rate, with successive windows overlapping every 8 points/input samples (resulting in 65 linear channels spaced 125 Hz apart), and using an update rate of 1000 Hz.

Figure 4C:
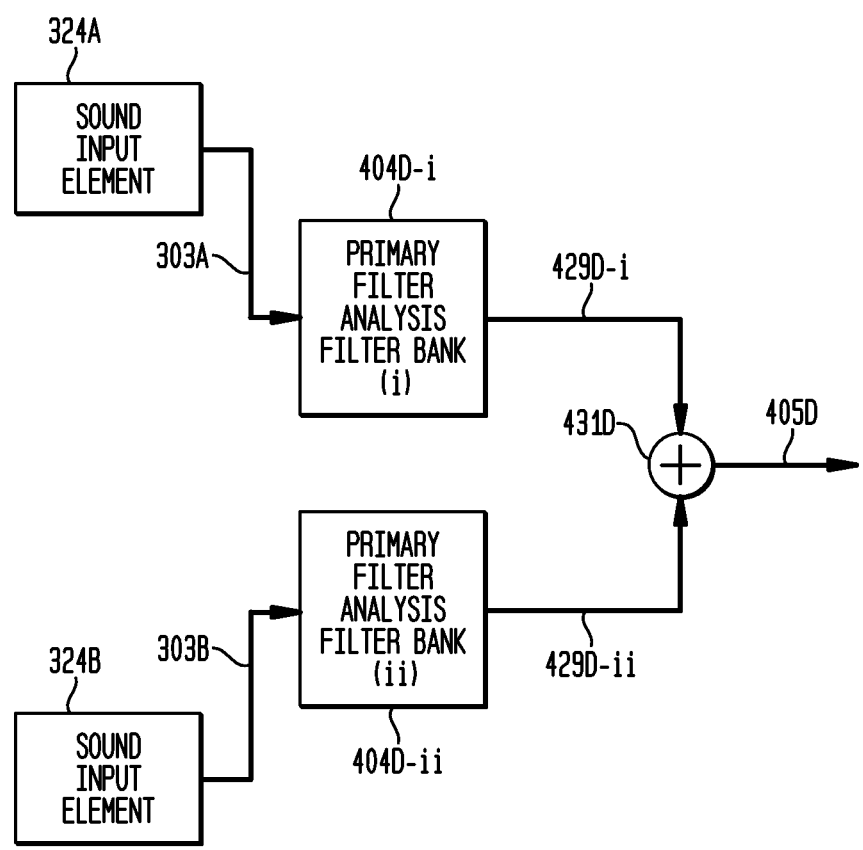
FIG. 4C is a functional block diagram of an alternative front end arrangement of the common stage of FIG. 4B, in accordance with some embodiments of the present technology.

FIG. 4C is a functional block diagram of an alternative front end arrangement of common stage 350D of FIG. 4B, in accordance with some embodiments of the present technology. In FIG. 4C (relative to FIG. 4B), pre-processing block 402D has been eliminated, a second instance of primary analysis filter bank 404D has been added (resulting in filter banks 404D-i and 404D-ii) and a signal summation block 431D has been added. Signals 303A and 303B are provided to primary analysis filter bank 404D-i and primary analysis filter bank 404D-ii, respectively. Primary analysis filter banks 404D-i and 404D-ii are each configured to perform a frequency-analysis type of filtering that has both sufficient resolution in the frequency-domain and a sufficient update/analysis rate so that their output signals 429D-i and 429D-ii are suitable for use in all further processing. Signals 429D-i and 429D-ii are provided to, and combined at, block 431D, resulting in signals 405D. As discussed above, output signals 405D are suitable for use in all further processing, e.g., such that common signal set 305D (which is dependent on signals 405D) will be sufficient to avoid aliasing in first signal set 309D and second signal set 311D, respectively.

Returning to FIG. 6B, meso-processing block 406D can perform operations that are advantageously done in the frequency-domain (e.g., so as to operate on signals 405D output by primary analysis filter bank 404D). Examples of operations that can be performed by meso-processing block 406D include various types of multi-channel compression, dynamic range expansion, noise reduction and/or amplitude scaling. The output of meso-processing block 406D is common signal set 305D. The output of meso-processing block 406D is common signal set 305D. In the absence of optional meso-processing block 406D, common signal set 305D is the output of primary analysis filter bank 404D, i.e., is signals 405D.

As to the stimulator-specific stages of FIG. 4B, each of electrical stimulation stage 352D and mechanical stimulation stage 354D includes corresponding sub-analysis filter banks 412D and 422D, and optional corresponding meso-processing blocks 410D and 420D and optional corresponding post-processing blocks 414D and 424D, respectively. Meso-processing blocks 410D and 420D output signals 411D and 421D to sub-analysis filter banks 412D and 422D, respectively. Sub-analysis filter banks 412D and 422D output signals 413D and 423D to post-processing blocks 414D and 424D, respectively.

According to some embodiments of the present technology, the same operations are performed in corresponding meso-processing blocks 410D and 420D, sub-analysis filter banks 412D and 422D, and post-processing blocks 414D and 424D, albeit with different values of operational parameters thereof in order to reflect the different stimulators to which stimulator-specific stages 352D and 354D adapt signals, namely electrode assembly 318B and mechanical stimulation arrangement 315F, respectively. For example, the Adaptive Dynamic Range Optimization (ADRO®) type of automatic gain control, multi-channel noise reduction and/or frame/sampling rate conversions can be performed by meso-processing blocks 410D and 420D albeit using different values of operating parameters in order to adapt the processed signals to electrode assembly 318B and mechanical stimulation arrangement 315F, respectively. For example (and continuing the example begun above), electrical stimulation stage 352D can convert from the 1000 Hz update rate of primary analysis filter bank 404D to an update rate of 2400 Hz in order to support a rate of 2400 pulses/stimuli per second (pps) per electrode, while mechanical stimulation stage 354D can remain at the 1000 Hz update rate of primary analysis filter bank 404D. According to alternative embodiments of the present technology, at least one of corresponding meso-processing blocks 410D and 420D, sub-analysis filter banks 412D and 422D, and post-processing blocks 414D and 424D, respectively, differ in terms of at least operation performed therein.

Relative to a context in which one or more of the same operations are performed (albeit with different values of operational parameters thereof, as discussed above) (hereinafter, counterpart operations) in each of corresponding meso-processing blocks 410D and 420D and/or and in each of corresponding post-processing blocks 414D and 424D, according to other alternative embodiments of the present technology, at least one of corresponding meso-processing blocks 410D and 420D and/or and corresponding post-processing blocks 414D and 424D are configured to coordinate the timing of at least one of the counterpart operations performed therein, as indicated by two-headed arrows 440D and 442D, respectively.

Sub-analysis filter banks 412D and 422D select subsets of the frequency range bandwidth provided by primary analysis filter bank 404D, wherein such subsets are appropriate for adapting resulting signals 413D and 423D to electrode assembly 318B and mechanical stimulation arrangement 315F, respectively. For example, sub-analysis filter bank 412D can output signals in a range of about 2 kHz to about 8 kHz, and sub-analysis filter bank 422D can output signals in a range of about 0 Hz to about 2 kHz. Alternatively, sub-analysis filter banks 412D and 422D can be configured so that signals 413D and 423D have overlapping albeit different (i.e., not coextensive) frequency ranges.

The number of channels at the output of each of sub-analysis filter banks 412D and 422D and the associated channel widths are the result of having made different combinations of the channels generated by primary analysis filter bank 404D, i.e., are the result of having made different combinations of the channels present in common signal set 305D. Typically such combinations represent reductions in the number of channels relative to the number of channels present in common signal set 305D. For example (and continuing the example begun above), starting with the 65 channels provided by primary analysis filter bank 404D, sub-analysis filter bank 412D can use 8 of the 65 channels below about 2 kHz, while sub-analysis filter bank 422D can use 6 of the 65 channels above about 2 kHz.

Post-processing at locations along pipeline 368D subsequent to each of sub-analysis filter banks 412D and 422D allows stimulator-specific operations to be performed. For example, post-processing block 414D can perform maxima selection and mapping of maxima-amplitude to level-of-current for each electrode in electrode assembly 318B. Also, for example, post-processing block 424D can compression, dynamic range expansion, amplitude scaling and/maxima selection and mapping of maxima-amplitude to stroke amplitude for the vibrator in mechanical stimulation arrangement 315F.

Mechanical stimulation stage 354D optionally further includes a synthesis filter bank 426D that receives signals 425D from post-processing block 424D and outputs signals 311D. In synthesis filter bank 426D, e.g., an inverse FFT (IFFT) device can inversely transform signals 425D from the frequency domain back to the time domain in order to generate signals 311D. In the case of electrical stimulation stage 352D, a synthesis filter bank akin to synthesis filter bank 426D is not required. If synthesis filter bank 426D is not included, then signals 311D instead correspond to signals 425D.

In alternative embodiments of the present technology, primary analysis filter bank 404D and/or sub-analysis filter banks 412D and/or 422D can be configured with filter structures and related processing based on something other than FFT analysis. Other suitable filter structures and related processing can be based on Finite Impulse Response (FIR) analysis, Infinite Impulse Response (IIR) analysis, wavelet analysis, etc.

In other alternative embodiments of the present technology, pre-processing block 402D can process primarily in the frequency domain. As such, as a preliminary operation, pre-processing block 402D would transform time-domain signals 303A, 303B, etc. into the frequency domain before performing the processing mentioned above, namely one or more of broadband compression, dynamic range expansion, amplitude scaling (limiting/reducing or gaining), etc. In this embodiment, signals 403D would be in the frequency-domain already.

Figure 5:
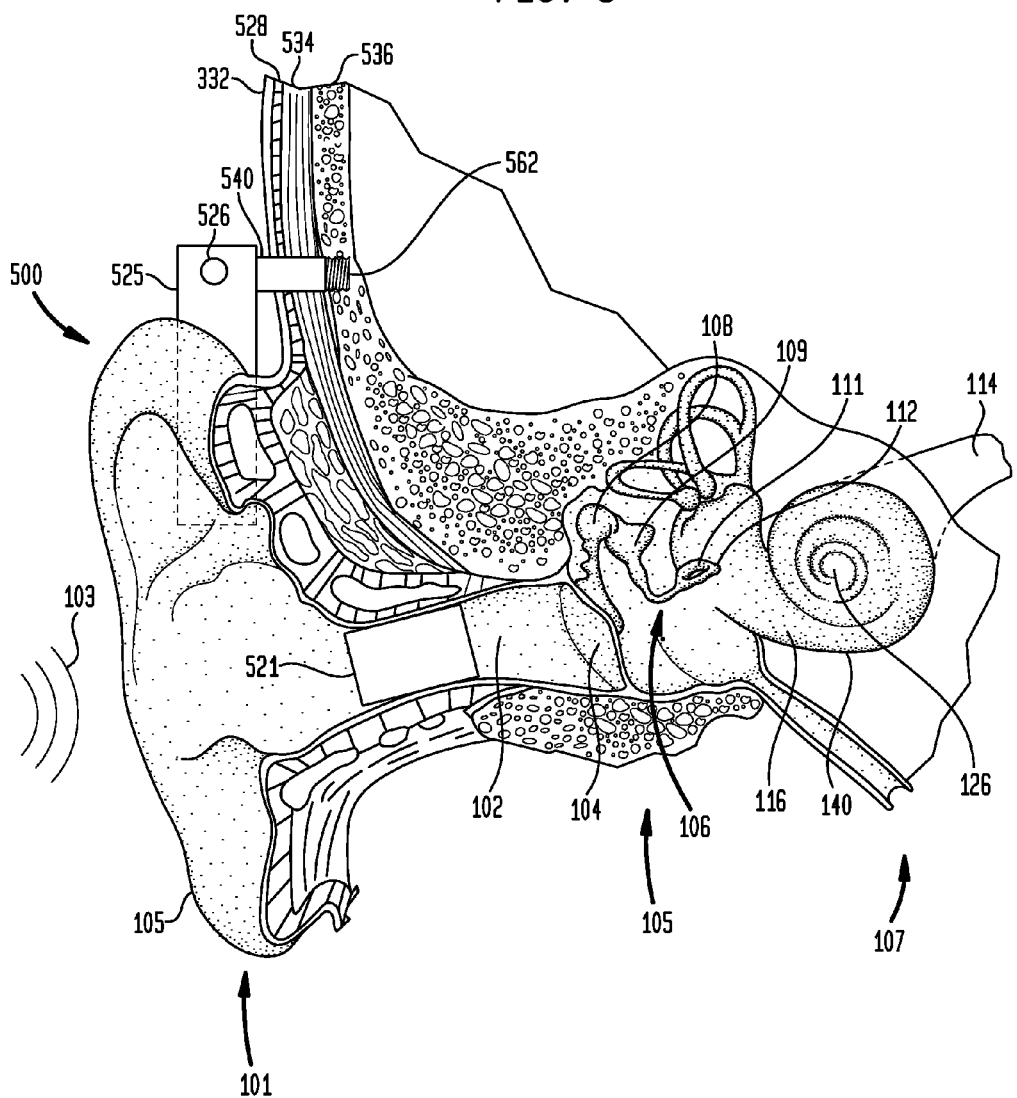
FIG. 5 is a perspective view of another hybrid auditory prosthesis, in which some embodiments of the present technology may be implemented.

FIG. 5 is a perspective view of another hybrid auditory prosthesis 500, in which some embodiments of the present technology can be implemented. Prosthesis 500 implements mechanical and acoustic stimulation modes of stimulation.

In FIG. 5, the different stimulation modes are each implemented in a respective series of components collectively referred to herein as stimulation modules. For example, the hybrid auditory prosthesis 500 provides vibrational stimulation generated by a bone conduction hearing module housed at least partially within housing 525 via implanted anchor 562 and the acoustic stimulation is generated by an acoustic hearing module 521. The vibrational stimulation FIG. 5 illustrates an example of the positioning of hybrid auditory prosthesis 500 relative to outer ear 101, middle ear 105 and inner ear 107 of a recipient of auditory prosthesis 500. Because they may share components, the stimulation module may not have the same components as hearing prostheses that conventionally provide the same type of stimulation.

In FIG. 5, hybrid auditory prosthesis 500 comprises a housing 525 with a microphone (not shown) positioned therein or thereon. Housing 525 is coupled to the body of the recipient via an anchoring system comprising coupling 540 and implanted anchor 562. As described below, hybrid auditory prosthesis 500 can comprise an external frequency domain (spectral) analysis module, an internal stimulation modules, e.g., a bone conduction stimulation module, and an acoustic stimulation module. The bone conduction stimulation module can comprise a bone-conduction processor, a transducer, transducer drive components, an anchoring system, and/or various other circuits/components. The anchor system can be fixed to bone 536. In various embodiments of the present technology, the anchor system may be surgically placed through skin 532, muscle 534 and/or fat 528. In certain embodiments of the present technology, the anchor system can comprise a coupling 540 and one or more anchoring elements 562. Also, in one embodiment of the present technology, an acoustic stimulation module can comprise an acoustic amplification module and an acoustic hearing module 521 for outputting an amplified acoustic sound.

The spiral ganglion cells that are responsible for the perception of high frequency sounds are generally located at the basal end of cochlea 540, i.e., that end of cochlea 540 closest to the oval window 112. For those individuals who suffer from high frequency hearing loss, the hair cells in the basal region of cochlea 540 are ineffective or otherwise damaged to the point where it is not possible to activate them. Hence, in accordance with one embodiment of the present technology, a hybrid auditory prosthesis 500 is positioned proximate to and retained by outer ear 101. Anchor 562 for the bone conduction module (not shown) is coupled to hybrid auditory prosthesis 500 and implanted in bone 536. The microphone signals are amplified and processed by an amplification module (not shown) in hybrid auditory prosthesis 500.

In certain embodiments of the present technology of the present technology, the transducer can comprise a piezoelectric element. The piezoelectric element converts an electrical signal applied thereto into a mechanical deformation (i.e. expansion or contraction) of the element. The amount of deformation of a piezoelectric element in response to an applied electrical signal depends on material properties of the element, orientation of the electric field with respect to the polarization direction of the element, geometry of the element, etc.

In some piezoelectric transducers, the maximum available transducer stroke is equivalent to the free stroke of the piezoelectric element. As such, some hybrid hearing prostheses utilizing these types of piezoelectric transducer have a limited transducer stroke and corresponding limits on the magnitude of the mechanical force that may be provided to the skull.

The acoustic stimulation module comprises an acoustic amplification processor, which is configured to amplify (positively or negatively) the received low-frequency component, and a speaker positioned sufficiently proximate to the recipient's hearing organs such that the amplified low-frequency component can be perceived by the recipient's residual hearing.

The in-the-canal hearing aid and its speaker or other output module 521 may be of conventional design and may be configured to receive and amplify the lower frequency components received, thereby presenting amplified acoustic waves (not shown) to tympanic membrane 104. Other designs for output module 521 may also be used in other embodiments of the present technology.

Figure 6A:
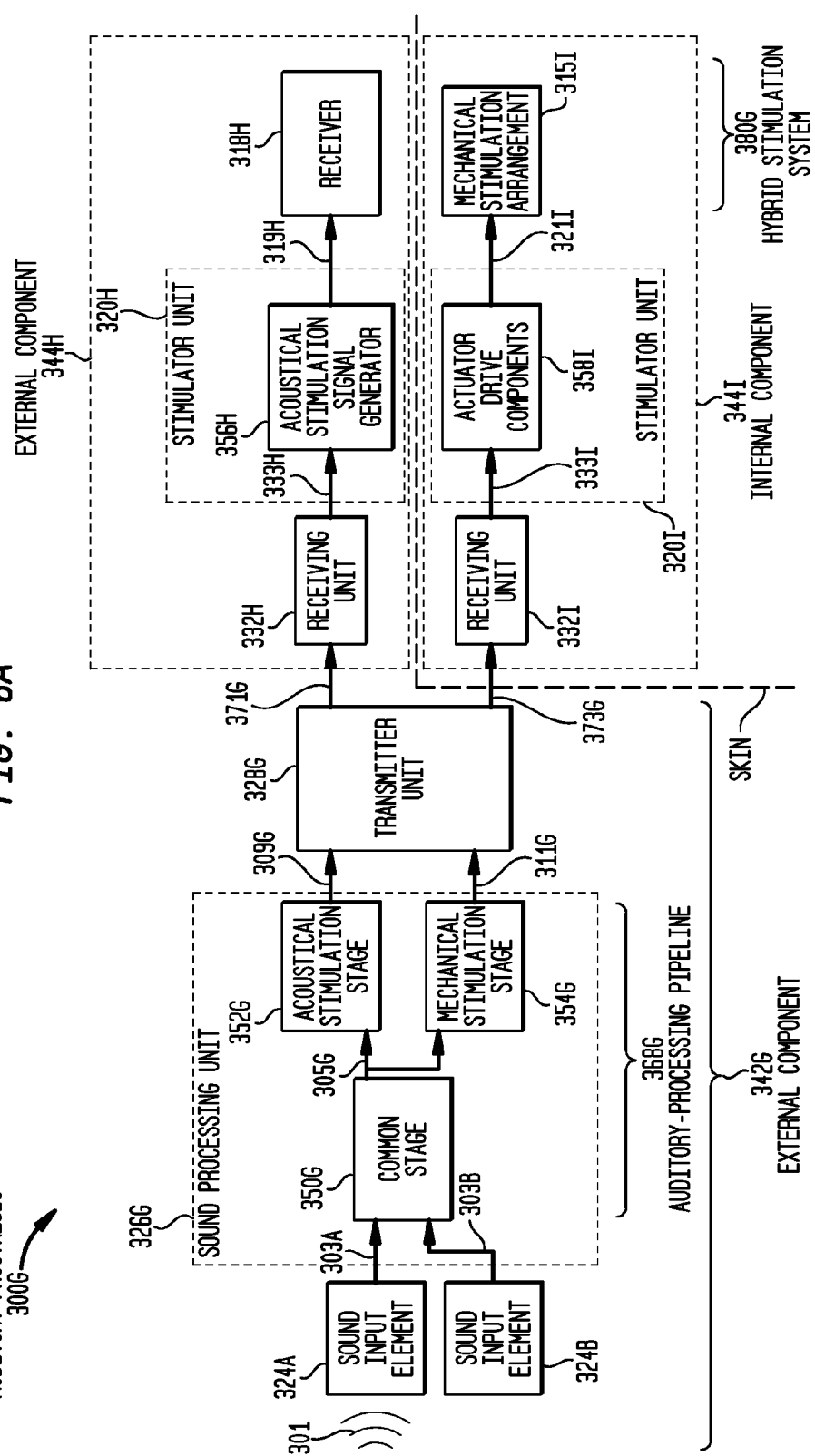
FIG. 6A is a functional block diagram illustrating the hybrid auditory prosthesis of FIG. 5 as being provided with another audio processing pipeline having a common stage and two or more stimulator-specific frequency-analysis stages, in accordance with some embodiments of the present technology.

FIG. 6A is a functional block diagram illustrating an embodiment of hybrid auditory prosthesis 500, referred to herein as hybrid auditory prosthesis 300G. In the illustrated embodiment, hybrid auditory prosthesis 300G comprises an external component 342G, an external component 344H and an internal component 344I. External component 342G comprises one or more sound input elements 326A, 326B, etc., for detecting sound, a sound processing unit 326G, a power source (not shown) and an external transmitter unit 328G.

One or more of sound input elements 326A, 326B, etc., receives a sound wave 301 and generates one or more electrical signals 303A, 303B, etc., representing the sound. Electrical signals 303A, 303B, etc., are provided to sound processing unit 326G which converts the signal(s) into encoded data signals which can be transmitted to internal component 344I.

More particularly, in FIG. 6A, one or more of electrical signals 303A, 303B, etc., is provided to a common stage 350G. In some embodiments of the present technology, common stage 350G performs filtering (in the frequency-domain) and processing of one or more of electrical signals 303A, 303B, etc., in a manner appropriate to the needs of the two or more different types of stimulation to be generated (as will be discussed in more detail below) and provides a common set of signals 305G to stimulator-specific stages, e.g., an acoustical stimulation stage 352G and a mechanical stimulation stage 354G. Acoustical stimulation stage 352G further filters (in the frequency domain) and processes common signal set 305G to generate a first set 309G of processed signals adapted for receiver 318H, e.g., wherein first signal set 309G corresponds to a low frequency portion of the audible frequency spectrum. Mechanical stimulation stage 354G further filters (in the frequency domain) and processes common signal set 305G to generate a second set 311G of processed signals adapted for mechanical stimulation arrangement 315F, e.g., wherein second signal set 311G corresponds to a low frequency portion of the audible frequency spectrum, which is perceivable by apical regions of a cochlea. It is noted that first signal set 309G is NOT adapted for mechanical stimulation arrangement 315F, and that second signal set 311G is NOT adapted for electrode assembly 318E.

Signals 309G and 311G are provided to transmitter unit 328G where the signals are encoded and transmitted, e.g., as RF signals 371G and 373G to receiving units 332H and 332I in external component 344H and internal component 344I, respectively. Receiving units 332H and 332I decode the transmitted signals, and provide electrical signals 333H and 333I to stimulator units 320H and 320I, respectively.

Based on electrical signals 333H and 333I, stimulator units 320H and 320I generate stimulation signals which are provided to one or more components of hybrid stimulation system 380G. As shown, hybrid stimulation system 380G comprises a receiver 318H and a mechanical stimulation arrangement 315F. Stimulator unit 320H comprises an acoustical stimulation signal generator 356H configured to generate acoustic stimulation signals 319H based on electrical signals 333H. Acoustic stimulation signals 319H are provided to receiver 318H for delivery to the recipient, thereby stimulating auditory nerve 114.

Stimulator unit 320I further comprises actuator drive components 358F. Based on signal 333I, actuator drive components 358F generate stimulation signals 321I which are provided to mechanical stimulation arrangement 315I. Stimulation signals 321I, sometimes referred to herein as actuator drive signals 321I, cause vibration of an actuator within mechanical stimulation arrangement 315I. As described above, in certain embodiments of the present technology, the actuator is coupled to the recipient's inner ear, the vibration is transferred to the inner ear fluid, thereby evoking a hearing percept by the recipient. In other embodiments of the present technology, the actuator is a positioned to deliver vibration to the recipient's skull. For example, the actuator may be part of an externally worn bone conduction device, or an implanted bone conduction device.

Although FIG. 6A has been described with reference to a hybrid auditory prosthesis 300G having external component 342G, in alternative embodiments of the present technology, it should be appreciated that component 342G can be implantable as well, e.g., integrated with internal component 344I. In such embodiments, sound processing unit 326G can be implanted in a recipient, e.g., in mastoid bone 119, such that sound processing unit 326G can communicate directly with stimulator unit 320I, thereby eliminating the portion of transmitter unit 328G that is provided for communication with receiving unit 332I, and eliminating receiving unit 332I as well. Similarly, external component 344H could be incorporated within external component 342G, thereby eliminating the portion of transmitter unit 328G that is provided for communication with receiving unit 318H, and eliminating receiving unit 318H as well.

Figure 6B:
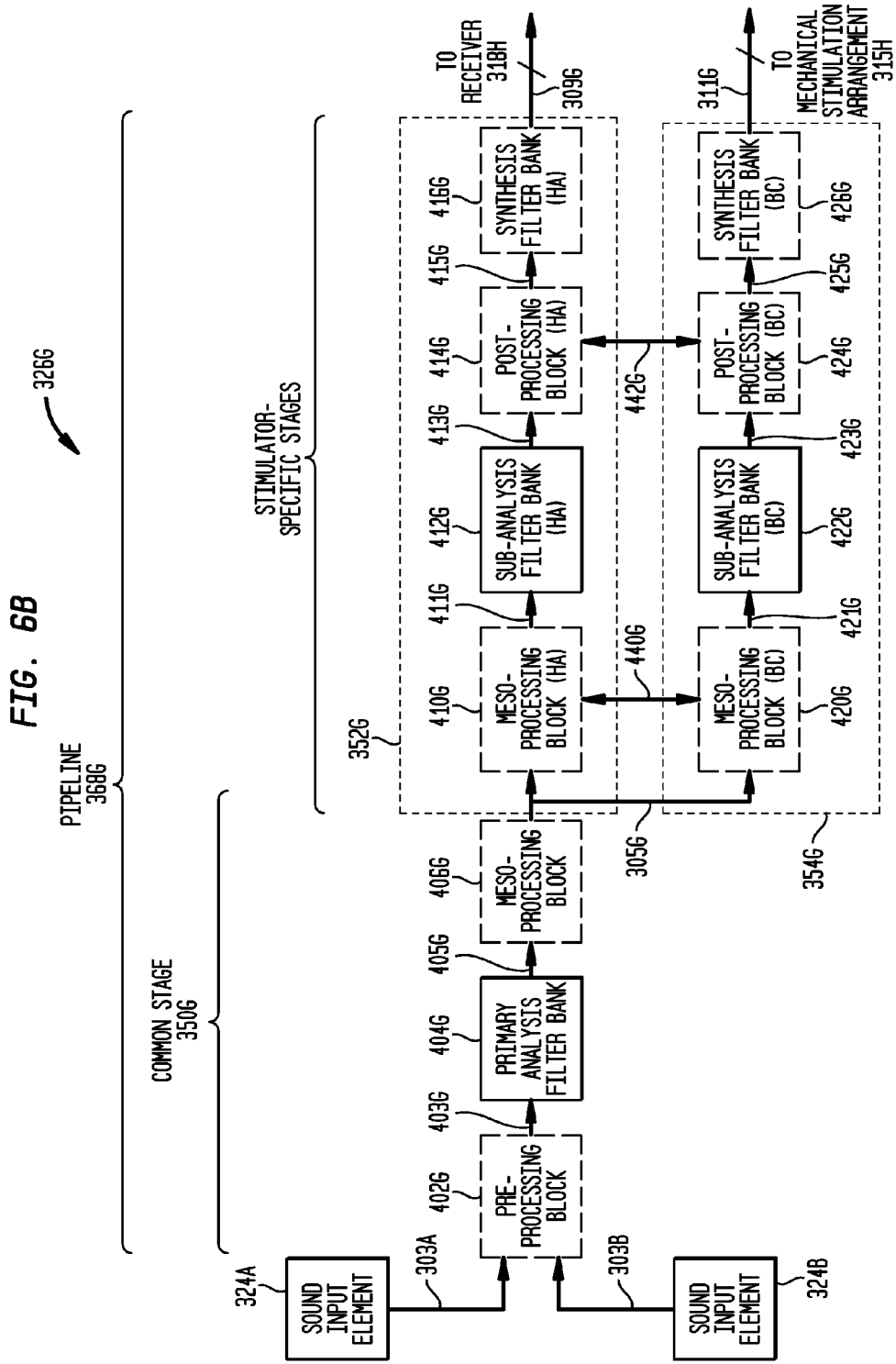
FIG. 6B is a functional block diagram of the audio-processing pipeline of FIG. 6A, in accordance with embodiments of the present technology.

FIG. 6B is a functional block diagram of audio-processing pipeline 368G included in sound processing unit 326G of hybrid auditory prosthesis 300G of FIG. 6A, in accordance with some embodiments of the present technology. Pipeline 368G includes common stage 350G and two stimulator-specific frequency-analysis stages 352G and 354G. Alternatively, additional stimulator-specific stages (not illustrated in FIG. 6B) can be provided in correspondence to additional types of stimulation (not illustrated in FIG. 6B) that may be provided.

In FIG. 6B, common stage 350G is illustrated as including a primary analysis filter bank 404G, and an optional pre-processing block 402G and an optional meso-processing block 406G. Values for operational parameters of common stage 350G, in particular, pre-processing block 402G, primary analysis filter bank 404G and meso-processing block 406G, are based in part on values for operational parameters used by acoustical stimulation stage 352G and mechanical stimulation stage 354G so as to avoid aliasing in first signal set 309G and second signal set 311G, respectively.

Pre-processing block 402G performs processing operations, e.g., time-domain multi-microphone processing (e.g., Zoom and Beam), that may be advantageous to perform in the time-domain, e.g., at least at a location along pipeline 368G before a signal representing sound wave 301 reaches primary analysis filter bank 404G. Other examples of pre-processing operations that can be performed by pre-processing block 402G include various types of broadband compression, dynamic range expansion, amplitude scaling (limiting/reducing or gaining), etc. Pre-processing block 402G outputs signals 403G to primary analysis filter bank 404G. For example, internally and after performing the time-domain processing, pre-processing block 402G can transform the signals being processed (e.g., signals 303A and 303B) into the frequency domain such that output signal 403G is a frequency-domain signal.

Primary analysis filter bank 404G is configured to perform a frequency-analysis type of filtering that has both sufficient resolution in the frequency-domain and a sufficient update/analysis rate so that its output signals 405G are suitable for use in all further processing, e.g., such that common signal set 305G (which is dependent on signals 405G) will be sufficient to avoid aliasing in first signal set 309G and second signal set 311G, respectively. Values for operational parameters of primary analysis filter bank 404G should be chosen with the specific hearing instrument outputs in mind, here (in the context of FIGS. 5, 6A and 6B) receiver 318H and mechanical stimulation arrangement 315H.

For example, primary analysis filter bank 404G can be configured with a Fast Fourier Transform (FFT) device that operates on a 128 point window (also referred to as a 128 input sample window) using a 16 kHz sampling rate, with successive windows overlapping every 8 points/input samples (resulting in 65 linear channels spaced 125 Hz apart), and using an update rate of 1000 Hz.

Figure 6C:
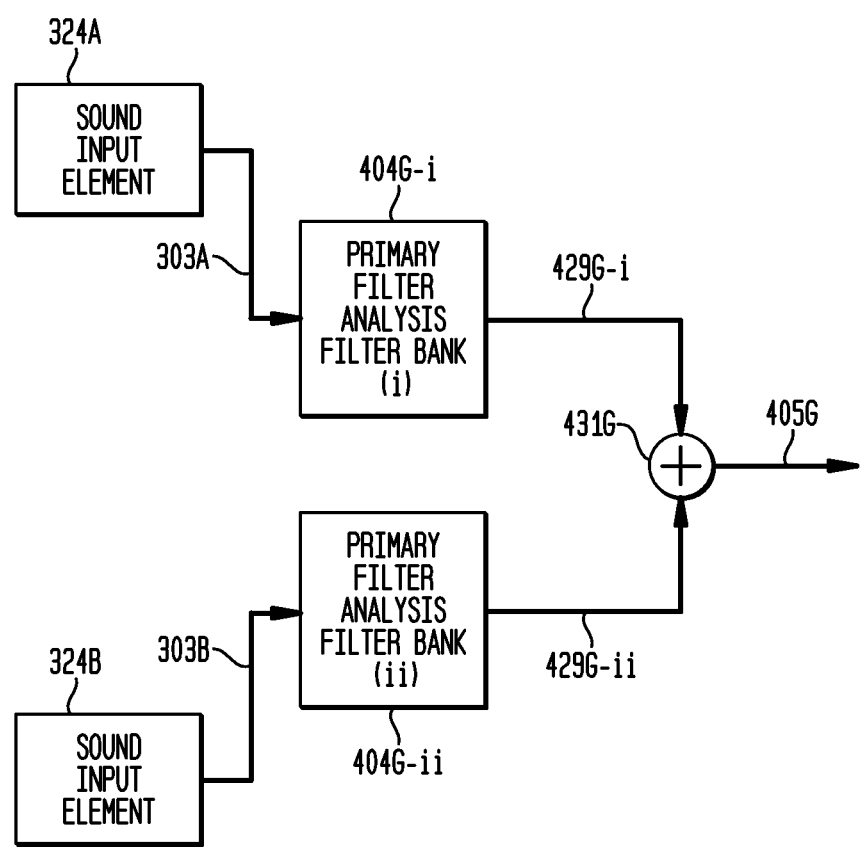
FIG. 6C is a functional block diagram of an alternative front end arrangement of the common stage of FIG. 6B, in accordance with some embodiments of the present technology.

FIG. 6C is a functional block diagram of an alternative front end arrangement of common stage 350G of FIG. 6B, in accordance with some embodiments of the present technology. In FIG. 4C (relative to FIG. 4B), pre-processing block 402G has been eliminated, a second instance of primary analysis filter bank 404G has been added (resulting in filter banks 404G-i and 404G-ii) and a signal summation block 431G has been added. Signals 303A and 303B are provided to primary analysis filter bank 404G-i and primary analysis filter bank 404G-ii, respectively. Primary analysis filter banks 404G-i and 404G-ii are each configured to perform a frequency-analysis type of filtering that has both sufficient resolution in the frequency-domain and a sufficient update/analysis rate so that their output signals 429G-i and 429G-ii are suitable for use in all further processing. Signals 429G-i and 429G-ii are provided to, and combined at, block 431G, resulting in signals 405G. As discussed above, output signals 405G are suitable for use in all further processing, e.g., such that common signal set 305G (which is dependent on signals 405G) will be sufficient to avoid aliasing in first signal set 309G and second signal set 311G, respectively.

Returning to FIG. 2B, meso-processing block 406G can perform operations that are advantageously done in the frequency-domain (e.g., so as to operate on signals 405G output by primary analysis filter bank 404G). Examples of operations that can be performed by meso-processing block 406G include various types of multi-channel compression, dynamic range expansion, noise reduction and/or amplitude scaling. The output of meso-processing block 406G is common signal set 305G. The output of meso-processing block 406G is common signal set 305G. In the absence of optional meso-processing block 406G, common signal set 305G is the output of primary analysis filter bank 404G, i.e., is signals 405G.

As to the stimulator-specific stages of FIG. 6B, each of acoustical stimulation stage 352G and mechanical stimulation stage 354G includes corresponding sub-analysis filter banks 412G and 422G, and optional corresponding meso-processing blocks 410G and 420G, and optional corresponding post-processing blocks 414G and 424G, respectively. Meso-processing blocks 410G and 420G output signals 411G and 421G to sub-analysis filter banks 412G and 422G, respectively. Sub-analysis filter banks 412G and 422G output signals 413G and 423G to post-processing blocks 414G and 424G, respectively.

According to some embodiments of the present technology, the same operations are performed in corresponding meso-processing blocks 410G and 420G, sub-analysis filter banks 412G and 422G, and post-processing blocks 414G and 424G, albeit with different values of operational parameters thereof in order to reflect the different stimulators to which stimulator-specific stages 352G and 354G adapt signals, namely receiver 318H and mechanical stimulation arrangement 315H, respectively. For example, the Adaptive Dynamic Range Optimization (AGRO®) type of automatic gain control, multi-channel noise reduction and/or frame/sampling rate conversions can be performed by meso-processing blocks 410G and 420G albeit using different values of operating parameters in order to adapt the processed signals to receiver 318H and mechanical stimulation arrangement 315H, respectively. For example (and continuing the example begun above), each of acoustical stimulation stage 352G and mechanical stimulation stage 354G can remain at the 1000 Hz update rate of primary analysis filter bank 404G. According to alternative embodiments of the present technology, at least one of corresponding meso-processing blocks 410G and 420G, sub-analysis filter banks 412G and 422G, and post-processing blocks 414G and 424G, respectively, differ in terms of at least operation performed therein.

Relative to a context in which one or more of the same operations are performed (albeit with different values of operational parameters thereof, as discussed above) (hereinafter, counterpart operations) in each of corresponding meso-processing blocks 410G and 420G and/or and in each of corresponding post-processing blocks 414G and 424G, according to other alternative embodiments of the present technology, at least one of corresponding meso-processing blocks 410G and 420G and/or and corresponding post-processing blocks 414G and 424G are configured to coordinate the timing of at least one of the counterpart operations performed therein, as indicated by two-headed arrows 440G and 442G, respectively.

Sub-analysis filter banks 412G and 422G select subsets of the frequency range bandwidth provided by primary analysis filter bank 404G, wherein such subsets are appropriate for adapting resulting signals 413G and 423G to receiver 318H and mechanical stimulation arrangement 315H, respectively. For example, sub-analysis filter bank 412G can output signals in a range of about 0 Hz to about 2 kHz, and sub-analysis filter bank 422G can output signals in a range of about 2 kHz to about 8 kHz. Alternatively, sub-analysis filter banks 412G and 422G can be configured so that signals 413G and 423G have overlapping albeit different (i.e., not coextensive) frequency ranges.

The number of channels at the output of each of sub-analysis filter banks 412G and 422G and the associated channel widths are the result of having made different combinations of the channels generated by primary analysis filter bank 404G, i.e., are the result of having made different combinations of the channels present in common signal set 305G. Typically such combinations represent reductions in the number of channels relative to the number of channels present in common signal set 305G. For example (and continuing the example begun above), starting with the 65 channels provided by primary analysis filter bank 404G, sub-analysis filter bank 412G can use 6 of the 65 channels above about 2 kHz, while sub-analysis filter bank 422G can use 8 of the 65 channels below about 2 kHz.

Post-processing at locations along pipeline 368G subsequent to each of sub-analysis filter banks 412G and 422G allows stimulator-specific operations to be performed. For example, post-processing block 414G can perform compression, dynamic range expansion and/or amplitude scaling for receiver 318H. Also, for example, post-processing block 424G can perform compression, dynamic range expansion, amplitude scaling and/maxima selection and mapping of maxima-amplitude to stroke amplitude for the vibrator in mechanical stimulation arrangement 315H.

Acoustic stimulation stage 352G optionally further includes a synthesis filter bank 416G that receives signals 415G from post-processing block 414G and outputs signals 311G. In synthesis filter bank 416G, e.g., an inverse FFT (IFFT) device, can inversely transform signals 415G from the frequency domain back to the time domain in order to generate signals 311G. If synthesis filter bank 416G is not included, then signals 311A instead correspond to signals 415G.

Mechanical stimulation stage 354G optionally further includes a synthesis filter bank 426G that receives signals 425G from post-processing block 424G and outputs signals 311G. In synthesis filter bank 426G, e.g., an inverse FFT (IFFT) device can inversely transform signals 425G from the frequency domain back to the time domain in order to generate signals 311G. If synthesis filter bank 426G is not included, then signals 311G instead correspond to signals 425G.

In alternative embodiments of the present technology, primary analysis filter bank 404G and/or sub-analysis filter banks 412G and/or 422G can be configured with filter structures and related processing based on something other than FFT analysis. Other suitable filter structures and related processing can be based on Finite Impulse Response (FIR) analysis, Infinite Impulse Response (IIR) analysis, wavelet analysis, etc.

In other alternative embodiments of the present technology, pre-processing block 402G can process primarily in the frequency domain. As such, as a preliminary operation, pre-processing block 402G would transform time-domain signals 303A, 303B, etc. into the frequency domain before performing the processing mentioned above, namely one or more of broadband compression, dynamic range expansion, amplitude scaling (limiting/reducing or gaining), etc. In this embodiment, signals 403G would be in the frequency-domain already.

FIG. 7 is a flowchart illustrating a method of processing an audio signal, in accordance with some embodiments of the present technology, the method being adapted for a hybrid auditory prosthesis that is provided at least two hearing stimulators of different types.

In FIG. 7, flow begins at step 702 and proceeds to step 704 at which one or more time-domain signals representing a sound wave are obtained. For example, such signals can correspond to signals 303A and 303B of FIG. 2B discussed above. Flow proceeds from step 704 to optional (as indicated by the phantom/dashed lines) step 706 at which the one or more time-domain signals are pre-processed, e.g., in the time domain. Such time-domain processing can correspond, e.g., to the processing that takes place in pre-processing block 402A of FIG. 2B discussed above. From step 706, flow proceeds to step 708 at which the pre-processed signals from step 706 (e.g., signals 403A in FIG. 2B) are commonly filtered in the frequency domain resulting in an initial version (e.g., signals 405A in FIG. 2B) of a common set of processed signals, e.g., common signal set 305A in FIG. 2B. Such common frequency-domain filtering can correspond, e.g., to the processing that takes place in primary analysis filter bank 404A of FIG. 2B, and is performed in a manner appropriate to the needs of the at least two hearing stimulators of different types that eventually will receive versions of the common set of processed signals. For example, the at least two hearing stimulators of different types can be electrode assembly 318E and receiver 315C of FIG. 2A.

Flow proceeds from step 708 to optional step 710 at which the initial version of the common set of processed signals is further processed (herein referred to as meso-processed) in the frequency domain resulting in the common set of processed signals. Such frequency-domain, meso-processing can correspond, e.g., to the processing that takes place in meso-processing block 406A of FIG. 2B. In the absence of optional meso-processing step 710, common signal set 305A is the output of common filtering step 708. Flow proceeds from step 710 to each of steps 712A and 712B.

In other words, up through step 710, flow had proceeded along a single, i.e., common, path. After step 710, however, flow branches into two counterpart stimulator-specific processing paths. One of the stimulator-specific paths (path A for stimulator A) includes step 714A and optional steps 712A and 716A. The other one of the stimulator-specific paths (path B for stimulator B) includes step 714B and optional steps 712B and 716B. Along path A, the common signal set is subjected to further filtering (in the frequency domain) and processing that results in a first set of processed signals, e.g., first set 309A of FIG. 2B, adapted for stimulator A, e.g., electrode assembly 318B. Along path B, the common signal set is subjected to further filtering (in the frequency domain) and processing that results in a second set of processed signals, e.g., second set 311A of FIG. 2B, adapted for stimulator B, e.g., receiver 315C.

Flow through stimulator-specific path A will be discussed, followed by a discussion of flow through stimulator-specific path B.

For stimulator-specific path A, at optional step 712A, the common signal set is subjected to stimulator-specific further processing (further meso-processing) in the frequency domain that begins adapting the common signal set to stimulator A. Such frequency-domain, meso-processing can correspond, e.g., to the processing that takes place in meso-processing block 410A of FIG. 2B.

From step 712A, flow proceeds to step 714A at which the meso-processed signals from step 712A (e.g., signals 411A in FIG. 2B) are stimulator-specifically filtered in the frequency domain resulting in an initial version (e.g., signals 413A in FIG. 2B) of a first set of processed signals, e.g., first signal set 309A in FIG. 2B. Such stimulator-specific frequency-domain filtering can correspond, e.g., to the processing that takes place in sub-analysis filter bank 412A of FIG. 2B, and is performed in a manner appropriate to the needs of stimulator A, e.g., electrode assembly 318B.

From step 714A, flow proceeds to optional step 716A at which the initial version of the first set of processed signals is further processed (herein referred to as post-processed) in the frequency domain resulting in the first set of processed signals. Such frequency-domain, post-processing can correspond, e.g., to the processing that takes place in post-processing block 414A of FIG. 2B. In the absence of optional post-processing step 716A, the common signal set 305A is the output of the stimulator-specific filtering step 714A. From step 716A, the first set of processed signals eventually is provided to stimulator A.

For stimulator-specific path B, at optional step 712B, the common signal set is subjected to stimulator-specific further processing (further meso-processing) in the frequency domain that begins adapting the common signal set to stimulator B. Such frequency-domain, meso-processing can correspond, e.g., to the processing that takes place in meso-processing block 420A of FIG. 2B.

From step 712B, flow proceeds to step 714B at which the meso-processed signals from step 712B (e.g., signals 421A in FIG. 2B) are stimulator-specifically filtered in the frequency domain resulting in an initial version (e.g., signals 423A in FIG. 2B) of a first set of processed signals, e.g., first signal set 311A in FIG. 2B. Such stimulator-specific frequency-domain filtering can correspond, e.g., to the processing that takes place in sub-analysis filter bank 422A of FIG. 2B, and is performed in a manner appropriate to the needs of stimulator B, e.g., receiver 315C.

From step 714B, flow proceeds to optional step 716B at which the initial version of the first set of processed signals is further processed (herein referred to as post-processed) in the frequency domain resulting in the second set of processed signals. Such frequency-domain, post-processing can correspond, e.g., to the processing that takes place in post-processing block 424A of FIG. 2B. Also, in the circumstance that the first set of processed signals would need to be returned to the time domain, e.g., where stimulator B is a receiver, e.g., receiver 315C, at step 716B the signals undergoing processing additionally can be inversely transformed from the frequency domain back into the time domain. Such additional processing can correspond, e.g., to the processing that takes place in synthesis filter bank 426A of FIG. 2B. In the absence of optional post-processing step 716B, the common signal set 305A is the output of the stimulator-specific filtering step 714B. From step 716B, the first set of processed signals eventually is provided to stimulator B.

The discussion of FIG. 7 has looked to FIGS. 2A-2B for examples. It should be appreciated that similar examples can be found in FIGS. 4A-4B and in FIGS. 6A-6B.

Embodiments of the present technology have been described herein in terms of partially and/or fully implantable hybrid auditory prostheses using dual-mode combinations of stimulation types in which the respective modes of stimulation are different. The dual modes combinations of different stimulation types illustrated in the example figures and discussed above include: electrical & acoustic stimulation; electrical & middle-ear mechanical stimulation; and acoustic & bone-conductive mechanical stimulation. It should be appreciated that alternative embodiments of the present technology may implement partially and/or fully implantable hybrid auditory prostheses using other dual-mode combinations of different stimulation types (by which to evoke a hearing percept in the recipient) including, but not limited to: optical stimulation and any one of electrical, acoustical, middle-ear mechanical and bone-conductive mechanical stimulation; electrical stimulation and bone-conductive mechanical stimulation; acoustical stimulation and middle-ear mechanical; and middle-ear mechanical stimulation and bone-conductive mechanical stimulation; and other different stimulation types (by which to evoke a hearing percept in the recipient) now known or later developed. It also should be appreciated that alternative embodiments of the present technology may implement partially and/or fully implantable hybrid auditory prostheses using tri-modes of stimulation, quad modes of stimulation, etc.

The present technology described and claimed herein is not to be limited in scope by the specific example embodiments herein disclosed, since these embodiments are intended as illustrations, and not limitations, of several aspects of the present technology. Any equivalent embodiments are intended to be within the scope of the present technology. Indeed, various modifications of the present technology in addition to those shown and described herein will become apparent to those skilled in the art from the foregoing description. Such modifications are also intended to fall within the scope of the appended claims.

What is claimed is:

1. An auditory prosthesis, comprising:
a first common filter bank configured to generate, based on an audio signal, a common set of processed signals;
a second filter bank configured to filter the common set of processed signals to generate a first set of stimulator-specific signals;
a third filter bank configured to filter the common set of processed signals to generate a second set of stimulator-specific signals;
a first hearing stimulator configured to provide to a recipient a first set of stimuli based on the first set of stimulator-specific signals, wherein each stimulus in the first set of stimuli is based on at least one stimulator-specific signal in the first set of stimulator-specific signals; and
a second hearing stimulator to provide to the recipient a second set of stimuli, wherein each stimulus in the second set of stimuli is based on at least one stimulator-specific signal in the second set of stimulator-specific signals.

2. The auditory prosthesis of claim 1, wherein a value of a parameter of the first common filter bank is based in part on a value of a parameter for each of second filter bank and the third filter bank so as to avoid, relative to common set of processed signals, aliasing in the first and second set of stimulator-specific signals.

3. The auditory prosthesis of claim 1, wherein the audio signal is a time-domain audio signal, and wherein the first common filter bank is configured to transform the time-domain audio signal into a frequency-domain audio signal.

4. The auditory prosthesis of claim 3, wherein the auditory prosthesis further comprises:
a time-domain signal processing unit configured to pre-process the time-domain audio signal prior to the first common filter bank generating the common set of processed signals.

5. The auditory prosthesis of claim 4, wherein the time-domain signal processing unit is configured to preprocess the time-domain audio signal by performing at least one of beam-forming, broadband compression, dynamic range expansion, or amplitude scaling.

6. The auditory prosthesis of claim 1, further comprising:
a frequency-domain transformer configured to transform the audio signal from the time-domain into the frequency-domain and provide the transformed audio signal to the first common filter bank.

7. The auditory prosthesis of claim 6, further comprising:
a frequency-domain signal processing unit configured to preprocess the transformed audio signal to provide a processed frequency-domain audio signal to the first common filter bank, wherein the first common filter bank is configured to generate the common set of processed signals based on the processed frequency-domain audio signal.

8. The auditory prosthesis of claim 7, wherein the frequency-domain signal processing unit is configured to process the frequency-domain audio signal by performing at least one of beam-forming, broadband compression, dynamic range expansion, or amplitude scaling.

9. The auditory prosthesis of claim 1, wherein each of the first common filter bank, the second filter bank, and the third filter bank includes at least one of a Fast Fourier Transform (FFT) unit, a wavelet transformer unit, a finite impulse response (FIR) unit, or an infinite impulse response (IIR) unit.

10. The auditory prosthesis of claim 1, wherein each of the first hearing stimulator and the second hearing stimulator is one of an acoustic-type hearing stimulator, a bone-conductive mechanical-type hearing stimulator, a middle-ear mechanical-type hearing stimulator, an electrical-type hearing stimulator, or an optical-type hearing stimulator.

11. A method of processing an audio signal in an auditory prosthesis, the method comprising:
generating a common set of signals by filtering, in the frequency domain, a frequency-domain audio signal with a common filter;
generating a first set of pre-filtered processed signals and a second set of pre-filtered processed signals by processing the common set of signals;
generating a first set of stimulator-specific signals by filtering, in the frequency domain, the first set of pre-filtered processed signals with a first stimulator-specific filter;
generating a second set of stimulator specific signals by filtering, in the frequency domain, the second set of pre-filtered processed signals with a second stimulator-specific filter;
causing a first stimulator to deliver to a recipient a first set of stimuli, wherein each stimulus in the first set of stimuli is based on at least one stimulation-specific signal in in the first set of stimulator-specific signals; and
causing a second stimulator to deliver to the recipient a second set of stimuli, wherein each stimulus in the second set of stimuli is based on at least one stimulation-specific signal in the second set of stimulator-specific signals.

12. The method of claim 11, wherein a value of a parameter of the common filter is based in part on a value of a parameter for each of first stimulator-specific filter and the second stimulator-specific filter, thereby avoiding, relative to the common set of signals, aliasing in the first set of stimulator-specific signals and aliasing in the second set of stimulator-specific signal.

13. The method of claim 11, wherein the method further comprises, before generating the common set of signals, transforming a time-domain audio signal into the frequency-domain audio signal.

14. The method of claim 13, wherein the method further comprises, before transforming the time-domain audio signal into the frequency-domain audio signal, preprocessing, in the time-domain, the time-domain audio signal.

15. The method of claim 13, wherein the method further comprises, before generating the common set of signals, preprocessing, in the frequency-domain, the frequency-domain audio signal.

16. The method of claim 13, wherein generating the first set of pre-filtered processed signals comprises processing the common set of signals using a first set of sound-processing functions, and wherein generating the second set of pre-filtered processed signals comprises processing the common set of signals using a second set of sound-processing functions.

17. The method of claim 16, wherein: generating the first set of pre-filtered processed signals comprises performing a common sound processing function, wherein a parameter of the common sound-processing function has a first value, and generating the second set of pre-filtered processed signals comprises performing the common sound-processing function, wherein the parameter has a second value that differs from the first value, and wherein the common sound processing function is included in each of the first set of sound-processing functions and the second set of sound-processing functions.

18. An auditory prosthesis, comprising:
a common stage configured to generate a common set of processed signals from an input audio signal, wherein the common stage includes a primary analysis filter bank;
a first stimulator-specific stage configured to generate, from the common set of processed signals, a first set of stimulator-specific signals, wherein the first stimulator-specific stage includes a first sub-analysis filter bank; and
a second stimulator-specific stage configured to generate, from the common set of processed signals, a second set of stimulator-specific signals, wherein the second stimulator-specific stage includes a second sub-analysis filter bank.

19. The auditory prosthesis of claim 18, further comprising:
first and second hearing stimulators each of different type, wherein the first hearing stimulator is configured to provide a recipient of the auditory prosthesis with a first set of stimuli based on the first set of stimulator-specific signals, and wherein the second hearing stimulator is configured to provide the recipient of the auditory prosthesis with a second set of stimuli based on the second set of stimulator-specific signals.

20. The auditory prosthesis of claim 19, wherein each of the first hearing stimulator and the second stimulator is one of an acoustic-type hearing stimulator, a bone-conductive mechanical-type hearing stimulator, a middle-ear mechanical-type hearing stimulator, an electrical-type hearing stimulator, or an optical-type hearing stimulator.

21. The auditory prosthesis of claim 18, wherein a value of a parameter of the primary analysis filter bank is based in part on a value of the parameter for each of the first sub-analysis filter bank and the second sub-analysis filter bank, thereby avoiding, relative to the common set of processed signals, aliasing in the first set of stimulator-specific signals and aliasing in the second set of stimulator-specific signal, respectively.

22. The auditory prosthesis of claim 18, wherein the input audio signal is a time-domain audio signal, and wherein primary analysis filter bank is configured to transform the time-domain audio signal into a frequency-domain audio signal.

23. The auditory prosthesis of claim 22, wherein the auditory prosthesis further comprises:
a time-domain signal processing unit configured to preprocess the time-domain audio signal prior to the primary analysis filter bank generating the common set of processed signals.

24. The auditory prosthesis of claim 23, wherein the time-domain signal processing unit is configured to preprocess the time-domain audio signal by performing at least one of beam-forming, broadband compression, dynamic range expansion, or amplitude scaling.

25. The auditory prosthesis of claim 18, further comprising:
a frequency-domain transformer configured to transform the input audio signal from the time-domain into the frequency-domain and provide a transformed audio signal to the primary analysis filter bank.

26. The auditory prosthesis of claim 25, further comprising:
a frequency-domain signal processing unit configured to preprocess the transformed audio signal and to provide a processed frequency-domain audio signal to the primary analysis filter bank, wherein the primary analysis filter bank is configured to generate the common set of processed signals based on the processed frequency-domain audio signal.

27. The auditory prosthesis of claim 26, wherein the frequency-domain signal processing unit is configured to process the frequency-domain audio signal by performing at least one of beam-forming, broadband compression, dynamic range expansion, or amplitude scaling.

28. The auditory prosthesis of claim 18, wherein each of the primary analysis filter bank, the first sub-analysis filter bank, and the second sub-analysis filter bank includes at least one of a Fast Fourier Transform (FFT) unit, a wavelet transformer unit, a finite impulse response (FIR) unit, or an infinite impulse response (IIR) unit.

* * * * *